US006838076B2

(12) United States Patent
Patton et al.

(10) Patent No.: US 6,838,076 B2
(45) Date of Patent: Jan. 4, 2005

(54) PULMONARY ADMINISTRATION OF CHEMICALLY MODIFIED INSULIN

(75) Inventors: John S. Patton, Los Altos, CA (US); Mei-Chang Kuo, Palo Alto, CA (US); J. Milton Harris, Huntsville, AL (US); Chester Leach, El Granada, CA (US); Kimberly Perkins, Belmont, CA (US); Blaine Bueche, Castro Valley, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 10/154,057

(22) Filed: May 21, 2002

(65) Prior Publication Data

US 2003/0118510 A1 Jun. 26, 2003

Related U.S. Application Data

(60) Provisional application No. 60/292,423, filed on May 21, 2001.

(51) Int. Cl.$^7$ ............................................... A61K 38/00
(52) U.S. Cl. ........................... 424/45; 424/46; 424/499
(58) Field of Search ........................... 424/45, 46, 499, 424/85.1, 486

(56) References Cited

U.S. PATENT DOCUMENTS

| | | | |
|---|---|---|---|
| 4,179,337 A | 12/1979 | Davis et al. | |
| 4,839,341 A | 6/1989 | Massey et al. | |
| 5,183,660 A | 2/1993 | Ikeda et al. | |
| 5,342,940 A | 8/1994 | Ono et al. | |
| 5,359,030 A | 10/1994 | Ekwuribe | |
| 5,438,040 A | 8/1995 | Ekwuribe | |
| 5,565,215 A | 10/1996 | Gref et al. | |
| 5,681,811 A | 10/1997 | Ekwuribe | |
| 5,730,990 A | 3/1998 | Greenwald et al. | |
| 5,766,897 A * | 6/1998 | Braxton ................... | 435/172.1 |
| 5,889,153 A | 3/1999 | Suzuki et al. | |
| 6,309,633 B1 | 10/2001 | Ekwuribe et al. | |
| 6,323,311 B1 * | 11/2001 | Liu et al. .................... | 530/303 |
| 6,427,681 B1 | 8/2002 | Gonda et al. | |

FOREIGN PATENT DOCUMENTS

| | | |
|---|---|---|
| EP | 0400472 | 4/1996 |
| WO | WO 94/20069 | 9/1994 |
| WO | WO 94/26778 | 11/1994 |
| WO | WO 97/04796 | 2/1997 |
| WO | WO 98/32466 | 7/1998 |
| WO | WO 99/21888 | 5/1999 |
| WO | WO 99/32134 | 7/1999 |
| WO | WO 00/06184 | 2/2000 |
| WO | WO 00/40203 | 7/2000 |
| WO | WO 00/78302 | 12/2000 |
| WO | WO 01/68141 | 9/2001 |
| WO | WO 02/092147 | 11/2002 |

OTHER PUBLICATIONS

Hinds et al. Synthesis and characterization of poly(ethylene glycol)insulin conjugates. Bioconjugate Chemistry. Mar.–Apr. 2000, 11(2): 195–201.*

F. Liu et al., "Bioactive Polyethylene Glycol Insulin Conjugates with Enhanced Stability.," Book of Abstracts. 213th ACS National Meeting, San Francisco, Apr. 13–17 (1997), POLY–223.

K. Hinds et al., "Bioactive Poly(Ethylene Glycol)–Insulin Conjugates with Enhanced Stability and Reduced Immunogenicity," Polymer Preprints (2000), vol. 41(1), p. 987–988.

M. Baudys et al., "Chemical Modification of Insulin to Enhance Its Physical Stability," Proceed. Intern. Symp. Control. Rel. Bioact. Mater. (1995), vol. 22, p. 538–539.

H. Zia et al., "Comparison of Nasal Insulin Powders Prepared by Supercritical Fluid and Freeze–Drying Techniques," Particulate Sci. Technol. (1997), vol. 15 (3–4), p. 273–301.

M. Baudys et al., "Design of Stable and Bioactive Insulin Conjugates," Book of Abstracts, 212th ACS National Meeting, Orlando, FL., Aug. 25–29, 1996, POLY–012.

M. Baudys et al., "Design of Stable and Bioactive Insulin Conjugates," Division of Polymer Chemistry, Inc., Polymer Preprints, vol. 37(2), Aug. 1996, p. 117–118, Papers Presented at the Orlando, FL. Meeting.

F. Liu et al., "Glucose–Induced Release of Glycosylpoly-(ethylene glycol) Insulin Bound to a Soluble Conjugate of Concanavalin A," Bioconjugate Chem. 1997, vol. 8, 8, p. 664–672.

Neubauer et al., "Influence of Polythylene Glycol Insulin on Lipid Tissues of Experimental Animals," Diabetes, vol. 32, Oct. 1983, p. 953–958.

F.M. Veronese et al., "PEG Peptide and Protein Drug Delivery: A Procedure to Identify the Peglation Site," Proc. Int. Symp. controlled Release Bioact. Mater. (1999), vol. 26, p. 106–107.

K. D. Hinds et al., "Poly(Ethylene Glycol) Conjugation to Improve the Physical and Biological Properties of Insulin," Proceed. Int'l. Symp. Control. Rel. Bioact. Mater., vol. 26, (Revised Jul. 1999) Controlled Release Society, Inc., p. 1072–1073.

T. Uchio et al, "Site–Specific Insulin Conjugates with Enhanced Stability and Extended Action Profile," Advanced Drug Delivery Reviews (1999), vol. 35, pp. 289–306.

(List continued on next page.)

Primary Examiner—Christopher R. Tate
Assistant Examiner—Maury Audet
(74) Attorney, Agent, or Firm—Susan T. Evans

(57) ABSTRACT

The present invention provides active, hydrophilic polymer-modified derivatives of insulin. The insulin derivatives of the invention are, in one aspect, suitable for delivery to the lung and exhibit pharmakokinetic and/or pharmacodynamic properties that are significantly improved over native insulin.

44 Claims, 14 Drawing Sheets

OTHER PUBLICATIONS

M. Ehrat et al., "Structural and Biological Properties of Polyoxyethylene–Insulin Adducts," IUPAC, Int'l Union of Pure and Applied Chem., 28th Macromolecular Symposium, Jul. 12–16, 1982, p. 351.

Caliceti et al., "Successful Insulin Delivery by PEG Conjugat ion," Proceed. Int'l Symp. Control. Rel. Bioact. Mater. 25 (1998) Controlled Release Society, Inc., p. 263–264.

K. Hinds et al., "Synthesis and Characterization of Poly(ethylene glycol)–Insulin Conjugates." Bioconjugate Chem. (2000), vol. 11, p. 195–201.

M. Ehrat et al., "Synthesis and Spectroscopic Characterization of Insulin Derivatives Containing One or Two Poly(ethylene oxide) Chains at Specific Positions," Biopolymers (1983), vol. 22, p. 569–573.

* cited by examiner

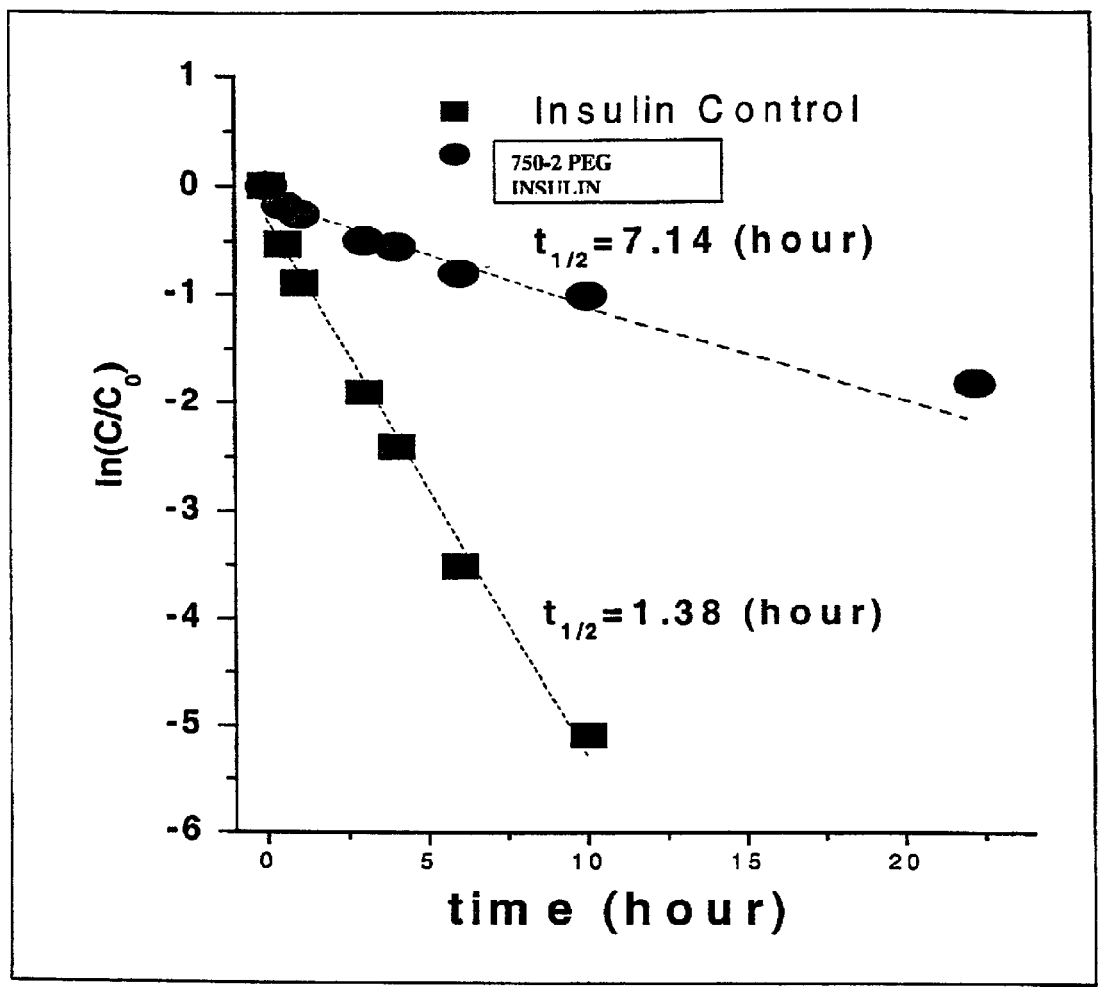
FIG. 1 Rate of Enzymatic Digestion of 750-2 PEG Insulin Versus an Unmodified Insulin Control

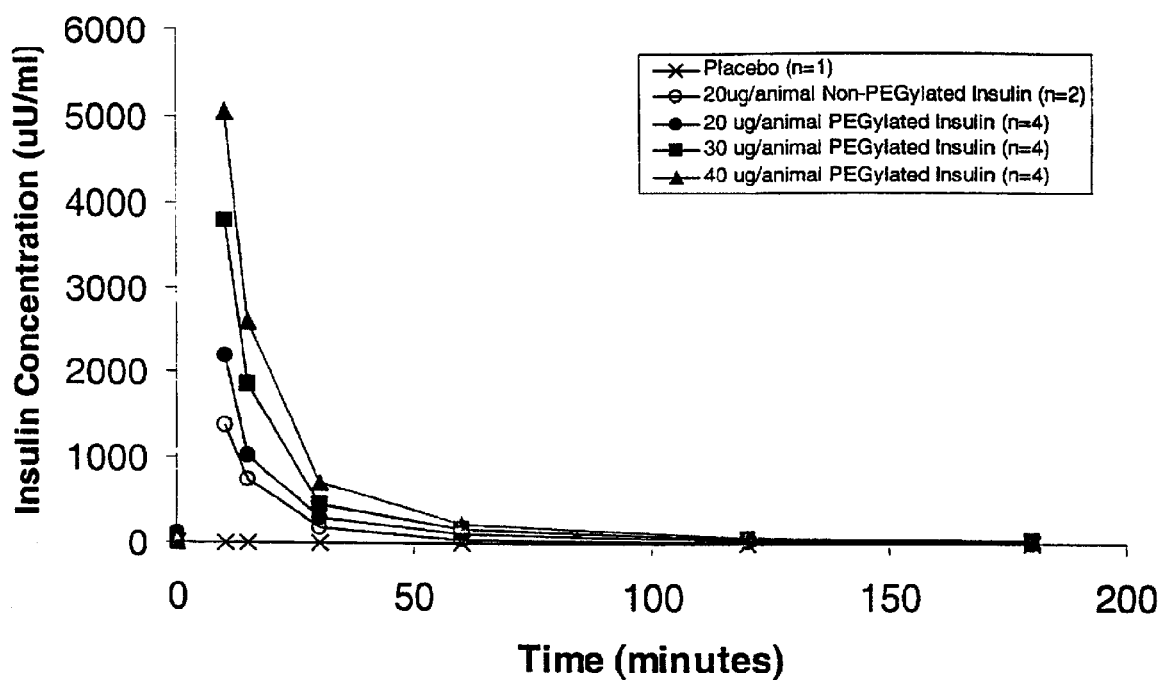
FIG. 2  IV Delivery of 5K PEG Insulin in Rats: Serum Clearance Profiles

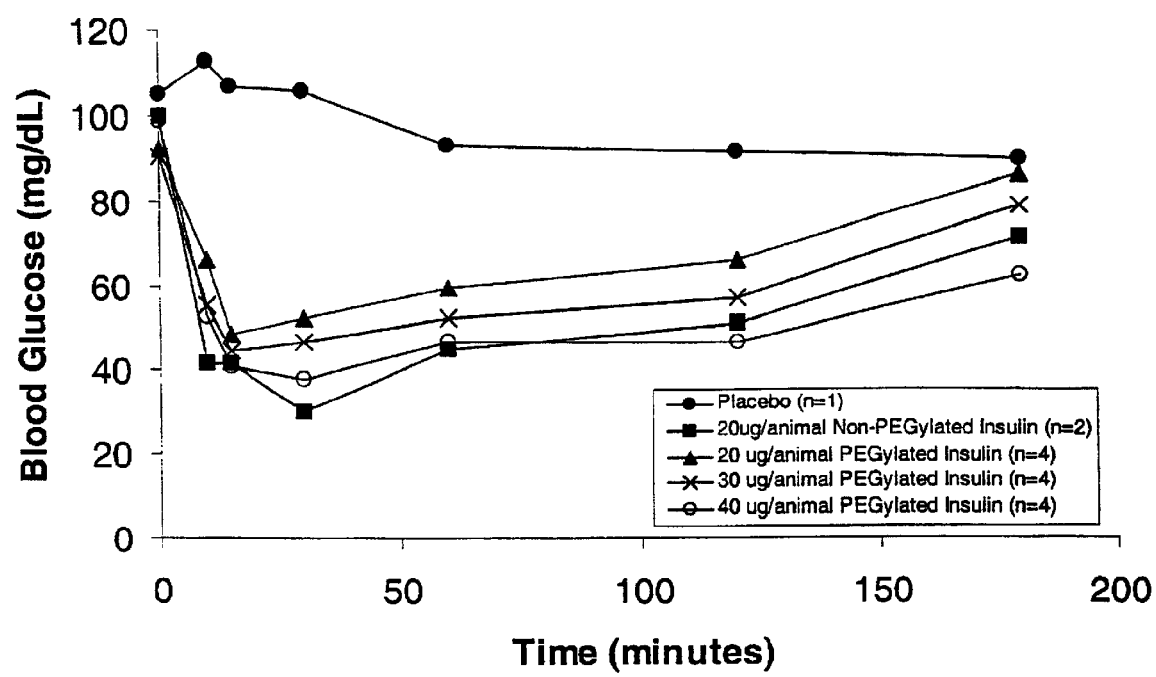
FIG. 3 IV Delivery of 5K PEG Insulin in Rats: Mean Blood Glucose Concentrations

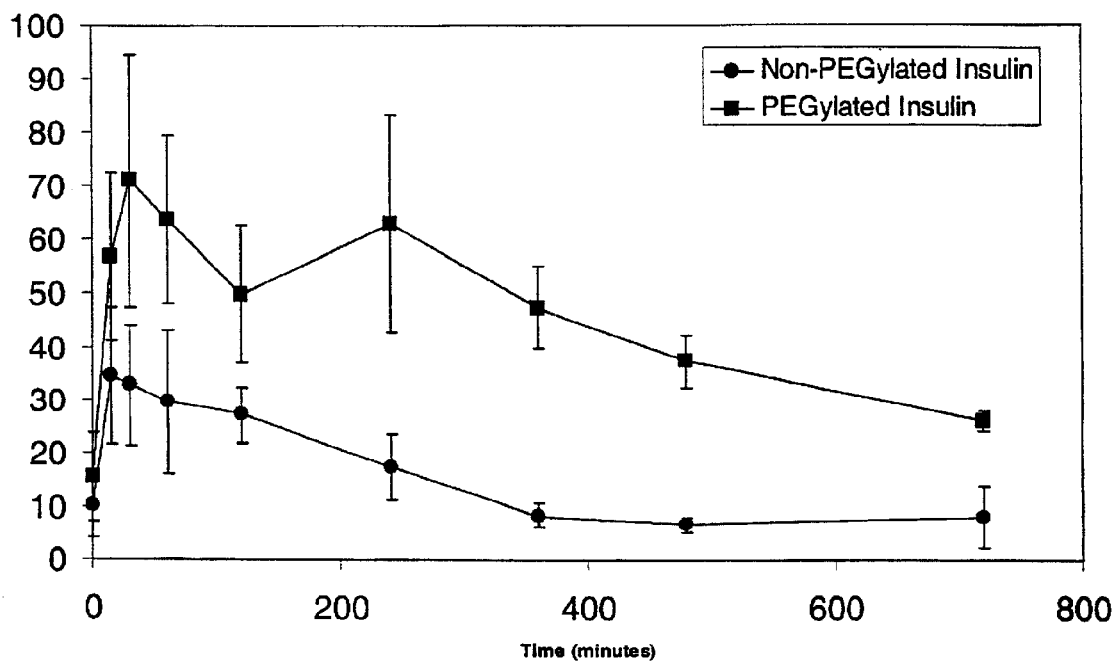
FIG. 4. IT Delivery of 5K PEG Insulin in Rats. Serum Clearance Profiles
(● = 40 μg/animal; ■ = 150 μg/animal)

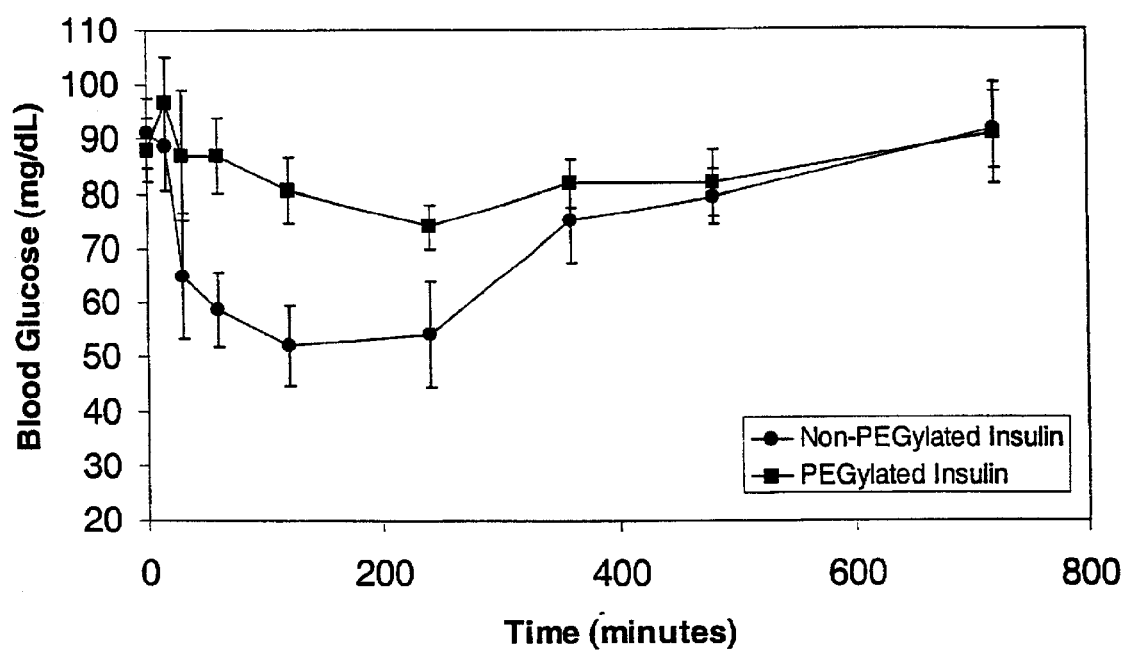
FIG. 5 IT Delivery of 5K PEG Insulin in Rats.
Mean Blood Glucose Concentrations
(● = 40 μg/animal; ■ = 150 μg/animal)

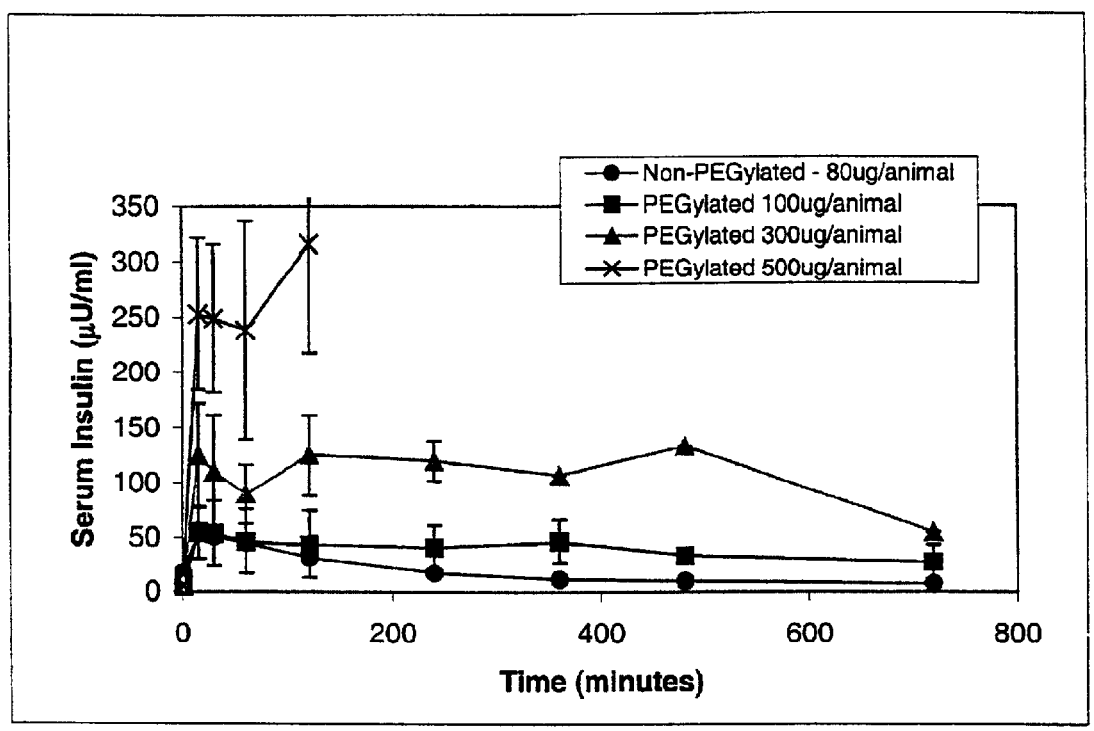
FIG. 6 IT Delivery of 750-1 PEG Insulin in Rats. Serum Clearance Profiles

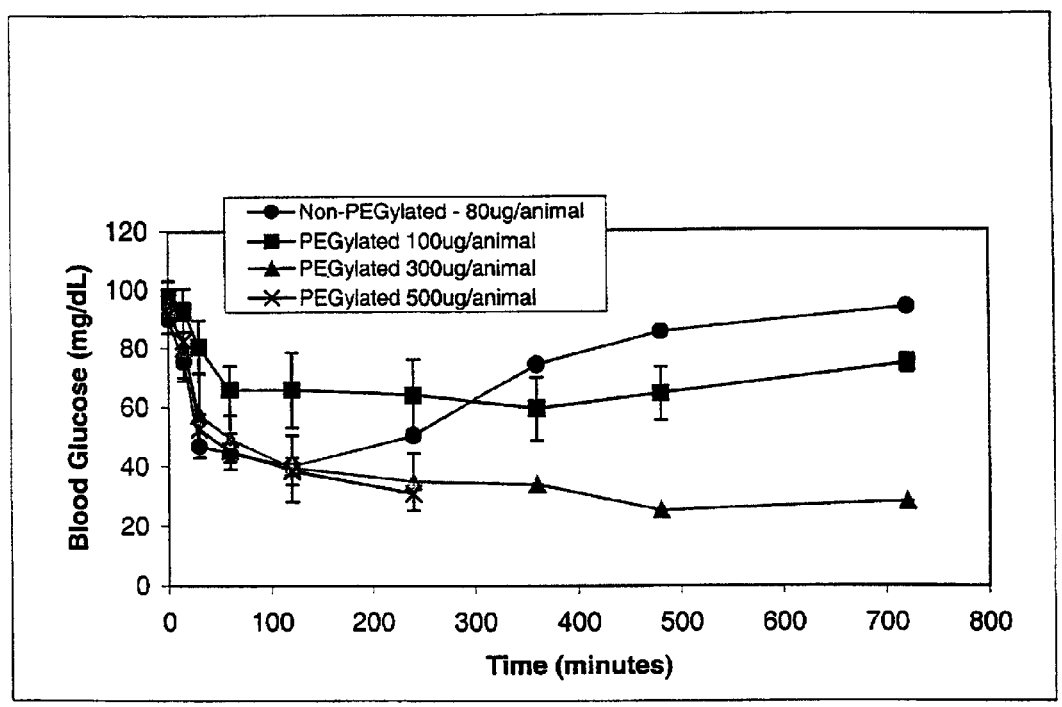
FIG. 7 IT Delivery of 750-1 PEG Insulin in Rats.
Mean Blood Glucose Concentrations

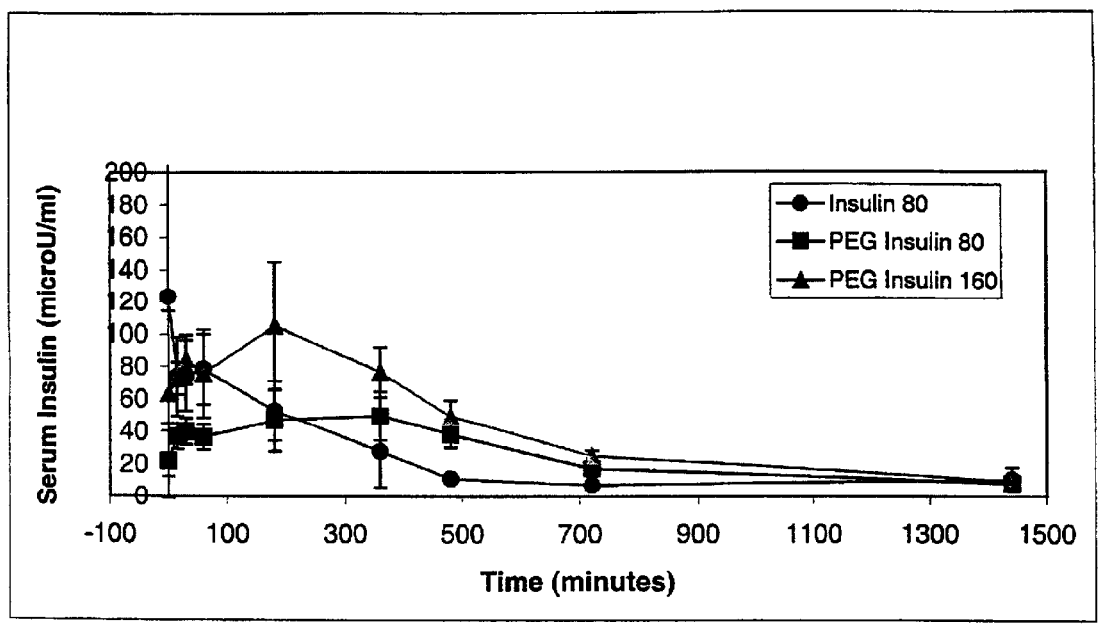
FIG. 8  IT Delivery of 750-1 PEG Insulin in Rats. Serum Clearance Profiles
(● = 80 μg/animal; ■ =80 μg/animal; ▲= 160 μg/animal)

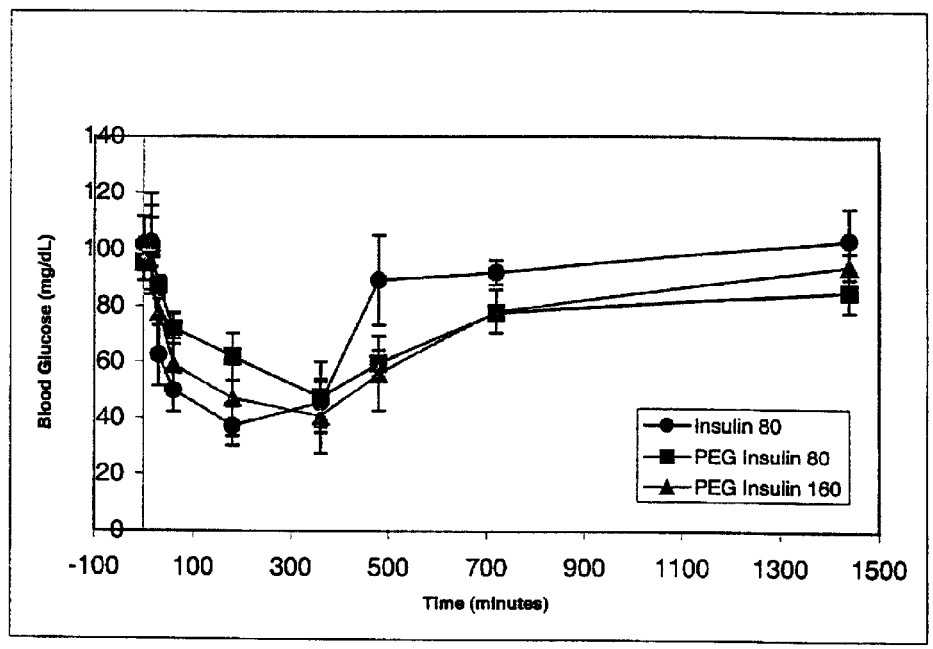
FIG. 9 IT Delivery of 750-1 PEG Insulin in Rats
(● = 80 µg/animal; ■ =80 µg/animal; ▲= 160 µg/animal)

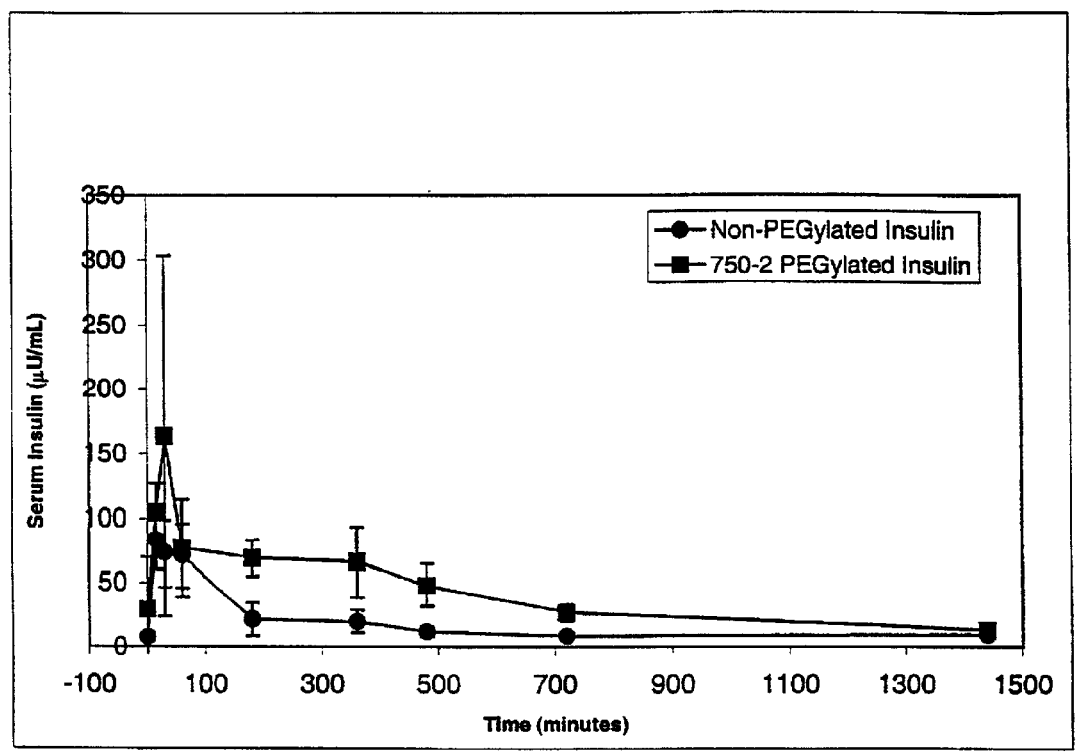
FIG. 10 IT Delivery of 750-2 PEG Insulin in Rats. Serum Clearance Profiles
(● = 80 μg/animal; ■ = 80 μg/animal)

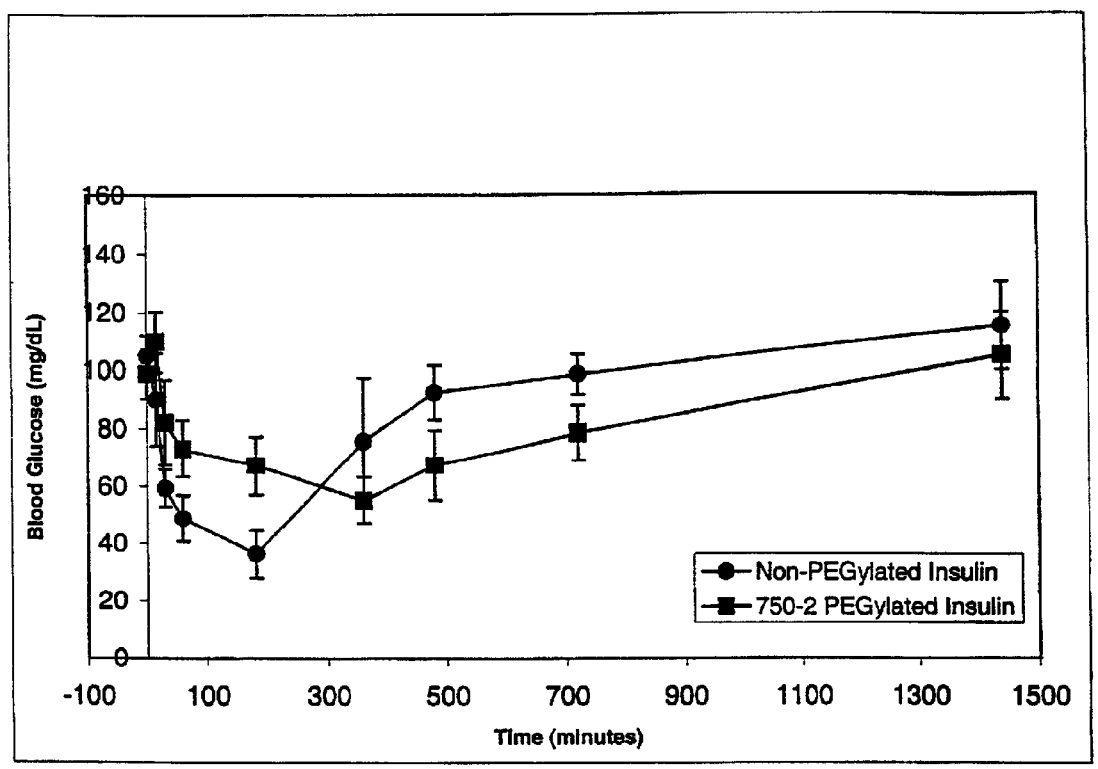
FIG. 11 IT Delivery of 750-2 PEG Insulin in Rats.
Mean Blood Glucose Concentrations
● = 80 μg/animal; ■ = 80 μg/animal)

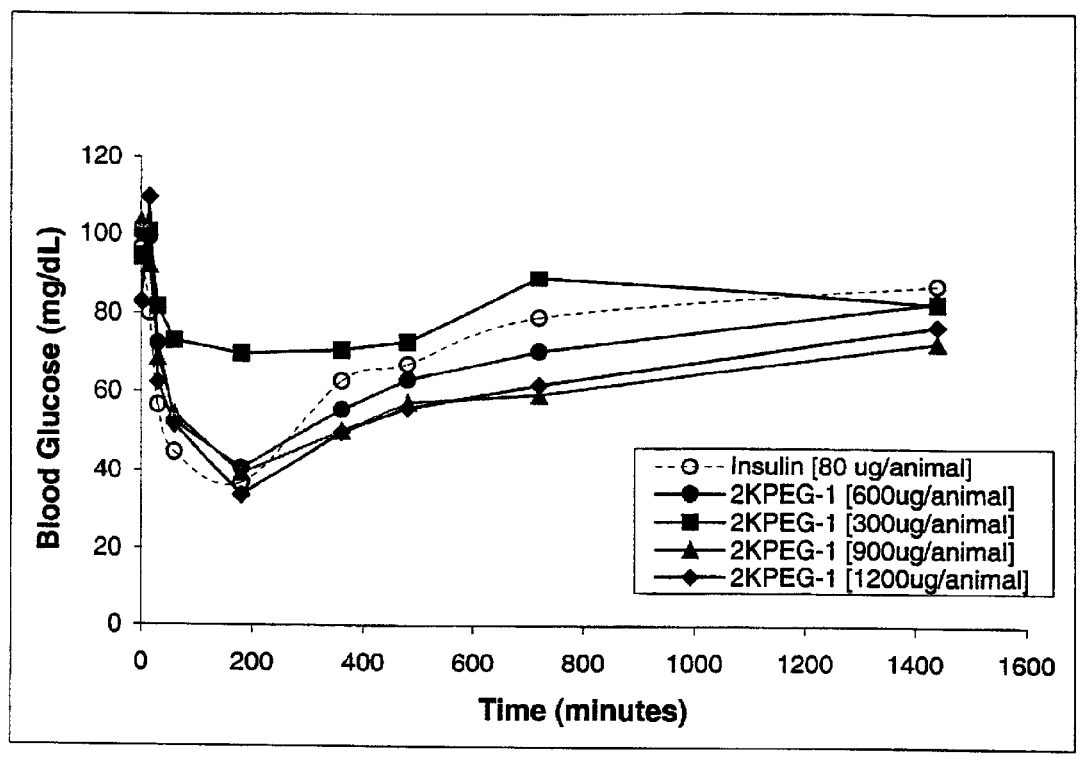
Fig. 12  IT Delivery of 2K PEG Insulin in Rats.
Mean Blood Glucose Concentrations

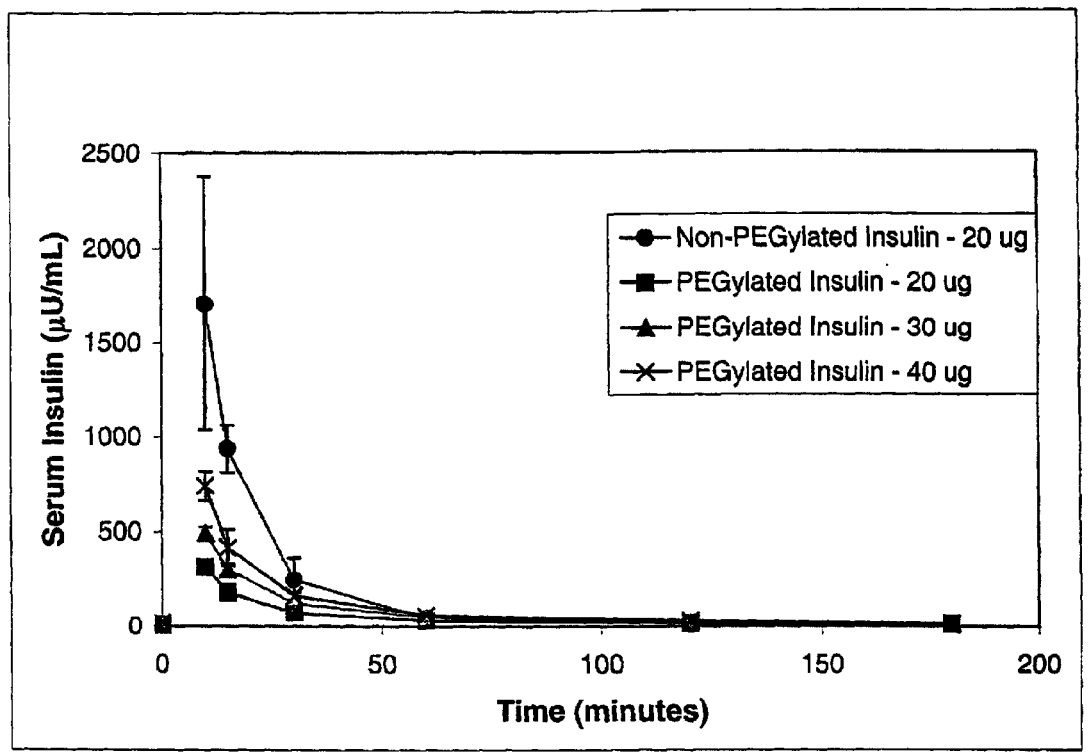
Fig. 13 IV Delivery of 2K Peg Insulin in Rats: Serum Clearance Profiles

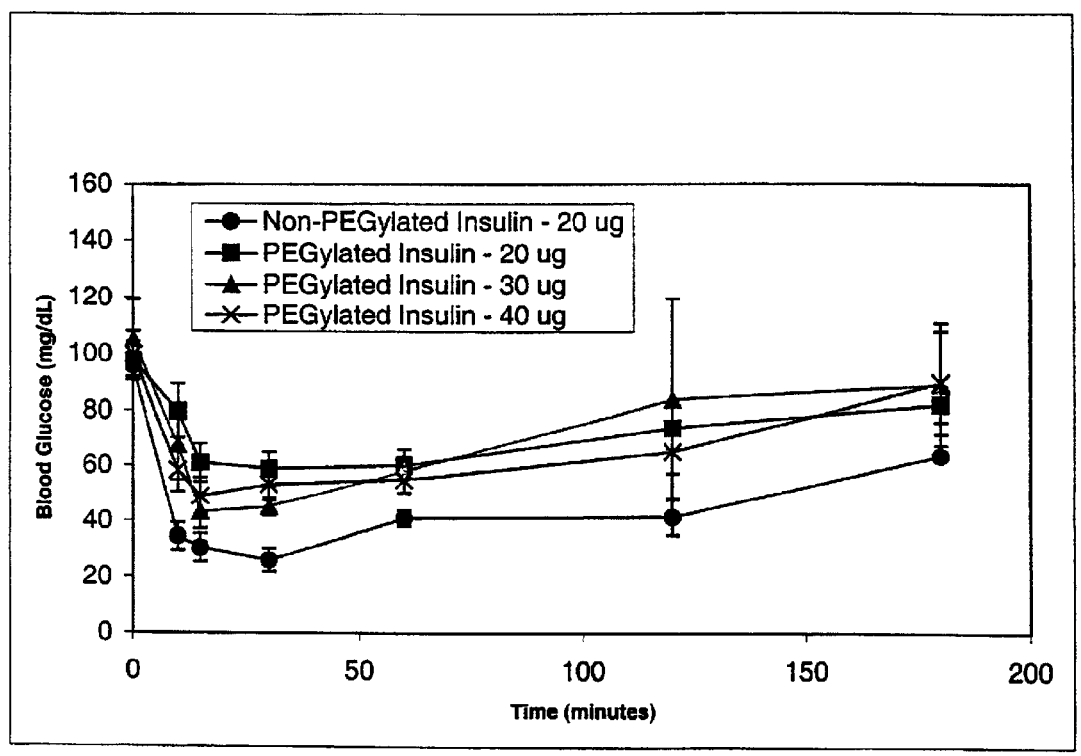
Fig. 14 IV Delivery of 2K PEG Insulin in Rats: Blood Glucose Concentrations

PULMONARY ADMINISTRATION OF CHEMICALLY MODIFIED INSULIN

This application claims the benefit of priority of U.S. Provisional patent application Ser. No. 60/292,423, filed May 21, 2001 the content of which is incorporated herein by reference in its entirety.

FIELD OF THE INVENTION

The present invention is directed to bioactive, hydrophilic polymer-modified insulin derivatives for delivery to the lung by inhalation. Methods for preparing and administering such derivatives are also provided.

BACKGROUND OF THE INVENTION

Insulin is a polypeptide hormone that is produced in the pancreatic β-cells of normal (non-diabetic) individuals. Human insulin is a 51 amino acid polypeptide hormone with a molecular weight of about 5800 daltons. The insulin molecule is composed of two peptide chains (an A and a B chain) containing one intrasubunit and two intersubunit disulfide bonds. The A chain is composed of 21 amino acids while the B chain is composed of 30 amino acids. The two chains of insulin form a highly ordered structure with several α-helical regions in both the A and the B chains. Interestingly, the isolated chains of insulin are inactive. In solution, insulin can exist as a monomer or as a dimer or as a hexamer. Insulin is hexameric in the highly concentrated preparations used for subcutaneous therapy but becomes monomeric as it is diluted in body fluids. Insulin is necessary for regulating carbohydrate metabolism by reducing blood glucose levels; a systemic deficiency of insulin causes diabetes. The survival of diabetic patients depends on the frequent and long-term administration of insulin to maintain acceptable blood glucose levels.

Current insulin formulations possess deficiencies that can lead to serious medical complications in the treatment of diabetes. For instance, the standard zinc insulin preparation most commonly used by diabetics exists as a suspension of microcrystals of inactive hexameric insulin. Dissolution of the microcrystals followed by dissociation of the hexamer into the active monomer form can lead to delayed and individually variable absorption of insulin into the bloodstream (F. Liu, et al., *Bioconjugate Chem.*, 8, 664–672 (1997); T. Uchio, et al., *Adv. Drug Del. Rev.*, 35, 289–306 (1999); K. Hinds, et al., *Bioconjugate Chem.*, 11, 195–201 (2000). Formulations of insulin also suffer from physical instability due to the tendency of insulin to form fibrils and insoluble precipitates. Precipitation is especially problematic for formulations intended for use in insulin pumps. Formulated insulin is also prone to chemical degradation, e.g., non-enzymatic deamidation and formation of high molecular weight transformation products such as covalent insulin dimers (Brange, J., et al., *Pharm. Res.*, 9, 715–726 (1992); Brange, J., et al., *Pharm. Res.*, 9, 727–734 (1992). There is significant evidence that the incidence of immunological responses to insulin may result from the presence of these covalent aggregates of insulin (Robbins, D.C., et al., *Diabetes*, 36, 838–841 (1987). Moreover, even highly purified human insulin is slightly immunogenic. (Kim, ibid.)

Apart from the formulation instability problems noted above, there are also numerous drawbacks associated with current insulin therapies from an administration standpoint. Insulin is most commonly administered by subcutaneous injection, typically into the abdomen or upper thighs. Insulin may also be administered intravenously or intramuscularly. In order to maintain acceptable blood glucose levels, it is often necessary to inject insulin at least once or twice per day, with supplemental injections of insulin being administered when necessary. Aggressive treatment of diabetes can require even more frequent injections, where the patient closely monitors blood glucose levels using a home diagnostic kit. The administration of insulin by injection is undesirable in a number of respects. First, many patients find it difficult and burdensome to inject themselves as frequently as necessary to maintain acceptable blood glucose levels. In fact, many Type 2 patients avoid going on insulin for years because of needle phobia. Such reluctance can lead to non-compliance, which in the most serious cases can be life-threatening. Moreover, systemic absorption of insulin from subcutaneous injection is relatively slow, frequently requiring from 45 to 90 minutes, even when fast-acting insulin formulations are employed. Thus, it has long been a goal to provide alternative insulin formulations and routes of administration which avoid the need for self-injection and which can provide rapid systemic availability of insulin.

Numerous non-injectable formulation types such as oral and nasal have been explored, however, no commercially viable oral or nasal-based delivery system for insulin has been developed as a result of these efforts (Patton, et al., *Adv. Drug Delivery Reviews*, 1, 35 (2–3), 235–247 (1999)), mainly due to very low and variable bioavailability (Hilsted, J., et al., *Diabetologia* 38, 680–684, (1995)). Although bioavailability can be increased with absorption enhancers, these agents can damage the mucosa.

However, inhaleable formulations of insulin have been developed which appear to be quite promising in overcoming many of the problems noted above. For example, U.S. Pat. No. 5,997,848 (Patton, et al., Inhale Therapeutic Systems, Inc.) describes dry powder formulations of insulin which (i) are chemically and physically stable at room temperature, and (ii) when inhaled, are rapidly absorbed through the epithelial cells of the alveolar region into the blood circulation. The rapid-acting insulin formulations and methods described therein avoid the need for burdensome self-injections, and have been shown in three month human efficacy studies to provide equivalent glucose control in Type I and Type II insulin-dependent diabetics when compared to subcutaneous injection (Patton, et al., *Adv. Drug Delivery Reviews*, 1, 35 (2–3), 235–247 (1999)). The dry powder insulin formulations described by Patton, et al., while overcoming the problems of formulation instability and patient non-compliance, still require frequent (e.g., mealtime) inhalations of insulin for effective control of glucose levels. Moreover, a typical insulin dosing regime of this type, based on rapid acting inhaleable insulin, still requires a single injection of long-acting insulin at bedtime for Type I and some Type II diabetics. Thus, there still exists a need for active, soluble, stable forms of insulin that require less frequent dosing, i.e., long-acting insulin formulations, preferably administrable by inhalation.

Long-acting insulin formulations are ideally characterized as having a very slow onset and a prolonged, relatively flat peak of action. Current long acting injectable insulin formulations, e.g., ultralente (extended insulin zinc suspension) and protamine zinc insulin suspension, are very unsatisfactory. These formulations tend to peak rather than provide a low basal concentration of insulin, are unpredictable, and typically exhibit a duration of action of no longer than about a day. The long half-life of ultralente insulin makes it difficult to determine the optimal dosage range, and protamine zinc insulin is rarely used because of its unpredictable and prolonged course of action (Goodman & Gilman, "The Pharmacological Basis of Therapeutics, Ninth Ed., Hardman and Limbird, eds, 1996, p. 1500). Other long-acting injectable formulations which have been explored unsuccessfully include albumin-bound insulin and cobalt-insulin hexamer formulations (Hoffman, A., Ziv E., Clin. Pharmacokinet, 33(4):285–301 (1997)).

A number of long-acting pulmonary insulin formulations have also been explored. These include liposomes containing a large excess of lipid relative to insulin (Liu. F-Y, et al., Pharm. Res. 10, 228–232, (1993)), porous poly(lactic acid-co-glycolic acid) (PLGA) insulin particles (Edwards, D. A., et al., Science 276(5320), 1868–1871 (1997)), nebulized PLGA nanospheres (Kawashima, Y., et al., J. Controlled Release, 62(1–2): 279–287 (1999)) and phospholipid/ protamine insulin formulations (Vanbever, R., et al., Proc. Control Rel. Bioact. Mater. 25, 261–262 (1998)). Unfortunately, all of these formulations have proven unsatisfactory, due to either low bioavailabilities when administered in rats, or due to formulation insufficiencies. Thus, a long-felt need exists for optimized long-acting insulin formulations that are bioactive, physically and chemically stable, water-soluble, and preferably monomeric. Ideally, such formulations will preferably be suited for pulmonary administration.

SUMMARY OF THE INVENTION

In one aspect, the present invention is based upon compositions of insulin for administration to the systemic circulation via the deep lung. Specifically, the compositions of the invention comprise a conjugate of insulin covalently coupled to one or more molecules of a non-naturally occurring hydrophilic polymer. In a preferred embodiment, the non-naturally occurring, hydrophilic polymer covalently coupled to insulin is a polyalkylene glycol such as polyethylene glycol (PEG), although all of the embodiments set forth herein may be equally applied to other non-naturally occurring hydrophilic polymers.

In general, an insulin-polymer conjugate of the invention will exhibit pharmacokinetic and pharmacodynamic properties improved over native insulin, particularly when administered to the lung. In one embodiment, the PEG-insulin conjugates provided herein exhibit good absolute bioavailabilities when administered to the lung and deep lung. In a particular embodiment, a PEG-insulin conjugate of the invention is characterized by an absolute pulmonary bioavailability that is greater than that of native insulin. Preferably, a PEG-insulin conjugate of the invention is characterized by having an absolute pulmonary bioavailability that is at least 1.5–2.0 times greater than that of native insulin. In a more preferred embodiment, a PEG-insulin conjugate in accordance with the invention is characterized by an absolute pulmonary bioavailability that is greater than about 15%, even more preferably greater than about 20% or most preferably greater than about 30%.

In yet another embodiment, a PEG-insulin conjugate of the invention, when administered pulmonarily, exhibits a Tmax (time required to reach maximum concentration) that is at least 1.5 times that of native insulin, or more preferably is at least 2 or 3 times, or even more preferably that is at least five times that of native insulin.

PEGs for use in the conjugates of the invention may possess several different features. In one embodiment of the invention, the polyethylene glycol-portion of a PEG-insulin conjugate as described herein is end-capped with an inert or non-reactive terminal group such as an alkoxy group or more specifically methoxy group.

In an alternative embodiment, the polyethylene glycol portion of the conjugate will possess an architecture particularly well suited for attachment to insulin including linear polyethylene glycols and multi-armed or branched polyethylene glycols. In yet another embodiment, a PEG-insulin conjugate may comprise two mono-functionally-derivatized insulin molecules interconnected by a di-activated polyethylene glycol (insulin-PEG-insulin). Alternatively, an insulin molecule within this "dumbell" architecture may be further modified by additional PEGs.

In another embodiment, a PEG-insulin conjugate of the invention comprises a forked polyethylene glycol having a branching moiety at one end of the polymer chain and two free reactive groups (or a multiple of two) linked to the branching moiety for covalent attachment to insulin. In this embodiment of the invention, the branched architecture of polyethylene glycol allows attachment of the polymer chain to two or more molecules of insulin.

The polyethylene glycol-portion of an insulin conjugate of the invention may optionally contain one or more degradable linkages.

Typically, insulin is covalently coupled to PEG via a linking moiety positioned at a terminus of the PEG. Preferred linking moieties for use in the invention include those suitable for coupling with reactive insulin amino groups such as N-hydroxysuccinimide active esters, active carbonates, aldehydes, and acetals.

In yet another embodiment, a PEG covalently coupled to insulin in a conjugate of the invention will comprise from about 2 to about 300 subunits of $(OCH_2CH_2)$, preferably from about 4 to 200 subunits, and more preferably from about 10 to 100 subunits.

In an alternative embodiment, a PEG covalently coupled to insulin will possess a nominal average molecular weight of from about 200 to about 10,000 daltons. In a preferred embodiment, the PEG will possess a nominal average molecular weight from about 200 to about 5000 daltons. In yet a more preferred embodiment, the PEG will possess a nominal average molecular weight from about 200 to about 2000 daltons or from about 200 to about 1000 daltons.

In a particular embodiment, the insulin portion of the conjugate comprises native human insulin.

In yet another embodiment, the conjugate of the composition of the invention possesses a purity of greater than about 90% (i.e., of the conjugate portion of the composition, 90% or more by weight comprises one or more PEG-insulins). That is to say, compositions of the invention may be characterized by a high degree of purity of conjugated insulin component, i.e., the composition is absent detectable amounts of free polyethylene glycol species and other PEG-related impurities.

In one embodiment, a composition of the invention comprises a conjugate wherein insulin is covalently coupled to PEG at one or more of its amino sites. Insulin contained within a composition of the invention may be mono-substitituted (i.e., having only one PEG covalently coupled thereto). Particular mono-substituted PEG-insulin conjugates in accordance with the invention possess a polyethylene glycol moiety covalently attached to a position on the insulin molecule selected from the group consisting of PheB1, GlyA1 and LysB29.

In a preferred embodiment, the PEG moiety is covalently attached at the PheB 1 site of insulin. In a one embodiment, at least about 75% of the B-1Phe sites on insulin are covalently coupled to PEG. In another embodiment, at least about 90% of the B-1 Phe sites on insulin are covalently coupled to PEG.

Compositions of the invention may also comprise a mixture of mono-conjugated and di-conjugated PEG insulin having any one or more of the features described above. Such compositions may further comprise a tri-conjugated PEG insulin.

In an alternative embodiment, a PEG insulin conjugate in accordance with the invention is characterized by a rate of proteolysis that is reduced relative to non-pegylated or native insulin.

A composition according to the invention may also comprise a mixture of a PEG-insulin conjugate and non-chemically modified or native insulin.

Also encompassed is a composition as described above in aerosolized form.

Compositions of the invention may be dissolved or suspended in liquid or in dry form, and may additionally comprise a pharmaceutically acceptable excipient.

Also provided herein is a bioactive polyethylene glycol-insulin conjugate suitable for administration by inhalation to the deep lung.

In yet another aspect, the invention provides a method for delivering a PEG-insulin conjugate to a mammalian subject in need thereof by administering by inhalation a PEG-insulin composition as previously described in aerosolized form.

The invention also provides in another aspect, a method for providing a substantially non-immunogenic insulin composition for administration to the lung. The method includes the steps of covalently coupling insulin to one or more molecules of a non-naturally occurring hydrophilic polymer conjugate as described herein, and administering the composition to the lung of subject by inhalation, whereby as a result, the insulin passes through the lung and enters into the blood circulation.

In another aspect, provided is a method for providing a prolonged effect insulin composition for administration to the lung of a human subject. The method includes covalently coupling insulin to one or more molecules of a non-naturally occurring hydrophilic polymer to provide a composition that includes an insulin-hydrophilic polymer conjugate, and administering the composition to the lung of the subject by inhalation. Upon the administering step, insulin passes through the lung and enters into the blood circulation and elevated blood levels of insulin are sustained for at least 8 hours post administration.

A PEG-insulin conjugate of the invention, when aerosolized and administered via inhalation, is useful in the treatment of diabetes melliltus (DM).

These and other objects and features of the invention will become more fully apparent when the following detailed description is read.

BRIEF DESCRIPTION OF THE FIGURES

FIG. 1 is a plot of the rate of enzymatic digestion of an illustrative PEG-insulin conjugate ("750-2 PEG insulin") versus an unmodified insulin control as described in detail in Example 6.

FIG. 2 is a plot of mean serum insulin concentrations following i.v. administration of illustrative compositions of pegylated (5K PEG Insulin) versus non-pegylated insulin (details are provided in Example 7);

FIG. 3 is a plot of blood glucose concentrations following i.v. administration of exemplary compositions of pegylated (5K PEG Insulin) versus non-pegylated insulin (details are provided in Example 7);

FIG. 4 is a plot of mean serum insulin concentrations following intratracheal instillation of pegylated (150 µg/animal, 5K PEG Insulin) versus non-pegylated human insulin (40 µg/animal) in male rats (Example 8);

FIG. 5. is a plot of mean blood glucose concentrations following intratracheal instillation of pegylated (150 µg/animal, 5K PEG Insulin) versus non-pegylated human insulin (40 µg/animal) in male rats (Example 8);

FIG. 6 is a plot of mean serum insulin concentrations following intratracheal instillation of pegylated (750-1 PEG Insulin) versus non-pegylated human insulin in male rats (Example 9);

FIG. 7. is a plot of mean blood glucose concentrations following intratracheal instillation of pegylated (750-1 PEG Insulin) versus non-pegylated human insulin in male rats (Example 9);

FIG. 8 is a plot of mean serum insulin concentrations following intratracheal instillation of pegylated (750-1 PEG Insulin, 80 and 160 µg/animal) versus non-pegylated human insulin (80 µg/animal) in male rats (Example 10);

FIG. 9. is a plot of mean blood glucose concentrations following intratracheal instillation of pegylated (750-1 PEG Insulin, 80 and 160 µg/animal) versus non-pegylated human insulin (80 µg/animal) in male rats (Example 10);

FIG. 10 is a plot of mean serum insulin concentrations following intratracheal instillation of pegylated (750-2 PEG Insulin, 80 µg/animal) versus non-pegylated human insulin (80 µg/animal) in male rats (Example 10);

FIG. 11. is a plot of mean blood glucose concentrations following intratracheal instillation of pegylated (750-1 PEG Insulin, 80 µg/animal) versus non-pegylated human insulin (80 µg/animal) in male rats (Example 11);

FIG. 12 is a plot of mean blood glucose concentrations following intratracheal instillation of pegylated (2K PEG Insulin, 300 µg/animal, 600 µg/animal, 900 µg/animal, and 1200 µg/animal) versus non-pegylated human insulin (80 µg/animal) in male rats (Example 12);

FIG. 13 is a plot of mean serum insulin concentrations following i.v. administration of an illustrative composition of pegylated (2K PEG Insulin) versus non-pegylated insulin (details are provided in Example 13); and FIG. 14 is a plot of blood glucose concentrations following i.v. administration of an exemplary composition of pegylated (2K PEG Insulin) versus non-pegylated insulin (details are provided in Example 13).

DETAILED DESCRIPTION OF THE INVENTION

The design, synthesis and characterization of various representative PEG-insulin conjugates have been optimized for pulmonary delivery to the lung. Although the preparation of PEG-insulin molecules has been previously described, the use of covalent coupling of PEG for providing prolonged action formulations of inhaleable insulin has not been previously demonstrated. In this regard, the challenge facing the applicants was to provide PEG-insulin conjugates having the optimal balance of number, location, structure, and molecular weight of PEG chains covalently attached to the insulin molecule to provide insulin compositions suitable for administration to the systemic circulation, preferably via the deep lung. Surprisingly, in light of the above, the inventors have discovered certain PEG- modified insulin formulations having one or more of the following features: (i) that are bioactive, i.e., that demonstrate at least about 5% of the activity of native insulin, or preferably have a bioactivity that is at least either substantially maintained or only minimally reduced from that of native insulin, or even more preferably, having an activity that is improved over native insulin, (ii) that are absorbed from the lung into the bloodstream (as opposed to "sticking" in the lung), (iii) that are chemically and physically stable, (iv) that, when administered to the lung, achieve blood levels of insulin that are elevated above baseline for at least about 8 hours post administration, (v) that are resistant to enzymatic attack by insulin-degrading enzymes, and (vi) that exhibit half lives that are extended over non-pegylated insulin when administered by inhalation, the details of which will become apparent when reading the following description.

I. Definitions

The following terms as used herein have the meanings indicated.

As used in the specification, and in the appended claims, the singular forms "a", "an", "the", include plural referents unless the context clearly dictates otherwise.

"Insulin" as used herein is meant to include proinsulin and encompasses any purified isolated polypeptide having part or all of the primary structural conformation (that is to say, contiguous series of amino acid residues) and at least one of the biological properties of naturally occurring insulin. In general, the term "insulin" is meant to encompass natural and synthetically-derived insulin including glycoforms thereof as well as analogs thereof including polypeptides having one or more amino acid modifications (deletions, insertions, or substitutions) to the extent that they substantially retain at least 80% or more of the therapeutic activity associated with full length insulin (prior to chemical modification with a hydrophilic, non-naturally occurring polymer as described herein). The insulins of the present invention may be produced by any standard manner including but not limited to pancreatic extraction, recombinant expression and in vitro polypeptide synthesis. Native or wild-type insulin refers to insulin having an amino acid sequence corresponding to the amino acid sequence of insulin as found in nature. Native or wild-type insulin can be natural (i.e., isolated from a natural source) or synthetically produced.

A "physiologically cleavable" or "degradable" bond is a weak bond that reacts with water (i.e., is hydrolyzed) under physiological conditions. Preferred are bonds that have a hydrolysis half life at pH 8, 25° C. of less than about 30 minutes. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon—carbon bonds (e.g., in aliphatic chains), ethers, amides, urethanes, and the like. Generally, a hydrolytically stable linkage is one that exhibits a rate of hydrolysis of less than about 1–2% per day under physiological conditions. Hydrolysis rates of representative chemical bonds can be found in most standard chemistry textbooks.

"PEG" or polyethylene glycol, as used herein, is meant to encompass any water-soluble poly(alkylene oxide). Most typically, PEGs for use in the present invention will contain the following structure, "—$CH_2CH_2O(CH_2CH_2O)_n CH_2CH_2$—, wherein the terminal groups or actual architecture of the overall PEG moiety may vary. One commonly employed PEG is end-capped PEG, wherein one terminus of the PEG is capped with a relatively inactive group, typically an alkoxy group such as methoxy (—$OCH_3$), while the other terminus is a hydroxyl group that can then be subjected to chemical modification. Specific PEG forms for use in preparing the insulin conjugates of the invention, such as branched, linear, forked PEGs, and the like, will be described in greater detail below.

"PEG-insulin conjugate" refers to an insulin molecule (as previously defined) having covalently linked or coupled thereto at least one polyethylene glycol moiety, and possessing any measurable degree of insulin activity (e.g., from about 2% to about 100% or more of the biological activity of native insulin).

"Nominal average molecular weight" in the context of a hydrophilic, non-naturally occurring polymer of the invention such as PEG, refers to the mass average molecular weight of polymer, typically determined by size exclusion chromatography, light scattering or intrinsic velocity in 1,2,4-trichlorobenzene. The polymers of the invention are typically polydisperse, possessing a low polydispersity value of less than about 1.05.

A "lipophilic moiety" is one which, when attached to a hydrophilic polymer in accordance with the invention, either by a degradable or non-degradable bond, is effective to substantially alter the hydrophilic nature of the polymer and thus the polymer-insulin conjugate. Typical lipophilic groups such as fatty acids will comprise from about 12–22 carbon atoms.

A "substantially non-immunogenic" insulin conjugate of the invention possesses a reduced immunogenicity relative to native insulin. Immunogenicity may be assessed by determining antibody titres in mice or preferably in rabbits upon administration of a PEG insulin conjugate relative to non-modified insulin.

"Alkyl" refers to hydrocarbon chains, typically ranging about 1 to 15 atoms in length. The hydrocarbon chains are preferably but not necessarily saturated and may optionally contain additional functional groups attached thereto. The hydrocarbon chains may be branched or straight chain. Exemplary alkyl groups include ethyl, propyl, 1-methylbutyl, 1-ethylpropyl and 3-methylpentyl. In one preferred embodiment of the invention, conjugates comprising an alkylated PEG, and in particular, a linear alkylated PEG, are those having an alkyl portion that is not a fatty acid or other lipophilic moiety.

"Lower alkyl" refers to an alkyl group containing from 1 to 5 carbon atoms, and may be straight chain or branched, as exemplified by methyl, ethyl, n-butyl, i-butyl, t-butyl.

"Absolute pulmonary bioavailability" is the percentage of a drug dose (e.g., of a PEG-insulin conjugate in accordance with the invention) delivered to the lungs that is absorbed and enters the blood circulation of a mammal relative to an intravenous dose of native insulin. Representative model systems for determining absolute pulmonary bioavailabilities include rat, dog, rabbit, and monkey. The inhaleable PEG-insulin compositions of the invention are, in one aspect, characterized by an absolute pulmonary bioavailability of at least about 20% in plasma or blood, with absolute pulmonary bioavailabilities generally ranging from about 10% to 30% or more. Generally, depending upon the specific nature of the PEG-insulin conjugate, a conjugate of the invention will possess an absolute pulmonary bioavailability of at least about one of the following: 10%, 12%, 15%, 18%, 20%, 22%, 25%, 30%, 32%, 35% or greater.

Absolute pulmonary bioavailability may be estimated by measuring absorption from direct intratracheal administration, instillation, or by inhalation of a PEG-insulin conjugate composition.

"Distribution phase", in reference to the half-life of a PEG-insulin conjugate, refers to the initial rapid phase during which insulin disappears from the plasma. The terminal slow or elimination phase half-life refers to the slow phase during which insulin is eliminated from the body.

"Prolonged effect" insulin refers to insulin having a duration of effect (i.e., elevated blood levels above baseline) of at least about 6 hours, preferably of at least about 8 hours.

"Glucose levels that are suppressed" refers to blood levels of glucose (e.g., after administration of a PEG-insulin conjugate of the invention) that are suppressed below baseline or basal levels.

"Pharmaceutically acceptable salt" includes but is not limited to amino acid salts, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, magnesium, aluminum, lithium, and ammonium (including substituted ammonium).

"Amino acid" refers to any compound containing both an amino group and a carboxylic acid group. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. An amino acid may be synthetic or naturally occurring, and may be used in either its racemic or optically active (D-, or L-) forms, including various ratios of enantiomers.

"Peptides" are composed of two or more amino acids joined by a peptide bond. Peptides can be homo- or hetero-peptides (i.e., composed of identical or different amino acid residues as defined above), and can vary in length from two amino acids to several hundred amino acids "Dry powder" refers to a powder composition that typically contains less than about 10% moisture.

A composition that is "suitable for pulmonary delivery" refers to a composition that is capable of being aerosolized and inhaled by a subject so that a portion of the aerosolized particles reach the lungs to permit penetration into the lower respiratory tract and alveoli. Such a composition is considered to be "respirable" or "inhaleable".

"Aerosolized" particles are liquid or solid particles that are suspended in a gas, typically as a result of actuation (or firing) of an inhalation device such as a dry powder inhaler, an atomizer, a metered dose inhaler, or a nebulizer.

"Emitted Dose" or "ED" provides an indication of the delivery of a drug formulation from a suitable inhaler device after a firing or dispersion event. More specifically, for dry powder formulations, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined using an in-vitro device set up which mimics patient dosing. To determine an ED value, a nominal dose of dry powder, typically in unit dose form, is placed into a suitable dry powder inhaler (such as that described in U.S. Pat. No. 5,785,049, assigned to Inhale Therapeutic Systems) which is then actuated, dispersing the powder. The resulting aerosol cloud is then drawn by vacuum from the device, where it is captured on a tared filter attached to the device mouthpiece. The amount of powder that reaches the filter constitutes the emitted dose. For example, for a 5 mg dry powder-containing dosage form placed into an inhalation device, if dispersion of the powder results in the recovery of 4 mg of powder on a tared filter as described above, then the emitted dose for the dry powder composition is: 4 mg (delivered dose)/5 mg (nominal dose)×100=80%. For non-homogenous powders, ED values provide an indication of the delivery of drug from an inhaler device after firing rather than of dry powder, and are based on amount of drug rather than on total powder weight. Similarly for MDI and nebulizer dosage forms, the ED corresponds to the percentage of drug which is drawn from a dosage form and which exits the mouthpiece of an inhaler device.

"Fine particle dose" or "FPD" is defined as the mass percent of powder particles having an aerodynamic diameter less than 3.3 μm, typically determined by measurement in an Andersen cascade impactor. This parameter provides an indication of the percent of particles having the greatest potential to reach the deep lung of a patient for systemic uptake of a drug substance.

A "dispersible" or "dispersive" powder is one having an ED value of at least about 30%, more preferably 40–50%, and even more preferably at least about 50–60% or greater.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size (e.g., electron microscopy, light scattering, laser diffraction).

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, in air, as the particle. The aerodynamic diameter encompasses particle shape, density and physical size of a particle. As used herein, MMAD refers to the midpoint or median of the aerodynamic particle size distribution of an aerosolized powder determined by cascade impaction, unless otherwise indicated.

"Pharmaceutically acceptable excipient or carrier" refers to an excipient that may optionally be included in the compositions of the invention. Preferred for compositions for inhalation are excipients that can be taken into the lungs with no significant adverse toxicological effects to the subject, and particularly to the lungs of the subject.

"Pharmacologically effective amount" or "physiologically effective amount" is the amount of a PEG-insulin conjugate present in a therapeutic composition as described herein that is needed to provide a desired level of insulin in the bloodstream to result in a target blood glucose level. The precise amount will depend upon numerous factors, e.g., the particular PEG-insulin, the delivery device employed, the components and physical characteristics of the therapeutic composition, intended patient population, patient considerations, and the like, and can readily be determined by one skilled in the art, based upon the information provided herein.

II. Hydrophilic, Non-Naturally Occurring Polymer-Insulin Conjugates

Several illustrative PEG-insulin conjugates in accordance with the invention have been prepared. Although polyethylene glycol is a preferred polymer for use in the conjugates of the invention, other water-soluble, hydrophilic, non-naturally occurring polymers may also be employed. Other polymers suitable for use in the invention include polyvinylpyrrolidone, polyvinylalcohol, polyacryloylmorpholine, polyoxazoline, and poly(oxyethylated polyols) such as poly(oxyethylated glycerol), poly(oxyethylated sorbitol), and poly(oxyethylated glucose). Polymers comprising subunits or blocks of subunits selected from the above-described water-soluble polymers may also be used. Additionally, Co-polymers of polyethylene glycol and polypropylene glycol may be employed. Polymers of the invention are preferably substantially absent fatty acid groups or other lipophilic moieties.

The following section illustrates that with the careful selection of one or more PEG moieties, pegylation reagents, insulin pegylation sites, pegylation conditions and subsequent conjugate purification, PEG-insulin compositions with the desired clinical properties (improved pharmacokinetic and/or pharmacodynamic properties) can be obtained. Specific features of the PEG-insulin conjugates of the invention will now be provided.

A. Structural Features of the Polymer and the Resulting Conjugate

A PEG-insulin conjugate of the invention will typically comprise one or more PEG chains each having a molecular weight ranging from about 200 to about 40,000 daltons, and preferably ranging from about 200 to about 10,000 daltons. Preferably, a PEG for use in the invention will possess an average molecular weight falling within one of the following ranges: from about 200 to 10,000 daltons, from about 200 to about 7500 daltons, from about 200 to about 6,000 daltons, from about 200 to about 5,000 daltons, from about 200 to about 3000 daltons, from about 200 to about 2000 daltons, and from about 200 to about 1000 daltons. Exemplary conjugates prepared with PEGs having molecular weights of 5,000 daltons, 2000 daltons and 750 daltons are provided in Examples 1–4.

Preferred PEG-insulins for administration to the lung will possess a PEG moiety having a molecular weight less than about 5000 daltons, preferably less than about 2000 daltons, and even less than about 1000 daltons. In one particular embodiment of the invention, the PEG-insulin conjugate possesses a PEG moiety having one of the following average molecular weights: 200, 300, 400, 500, 600, 750, 1000, 1500, 2000, 2500, 3000, 3500, 4000 or 5000. Higher molecular weight PEGs may, in certain instances, be less preferred due to a potential for loss of activity of the insulin molecule or, for pulmonary applications, reduced efficiency in crossing the lung (Example 8).

While lower molecular weight PEGs may be preferred for increasing bioavailability, high molecular weight PEG chains, e.g., having an average molecular weight of 5,000, 10,000, 15,000, 20,000, 25,000, 30,000 or 40,000 daltons or greater, although generally found to decrease the bioavailability of native insulin, may be preferred for increasing half-life, particularly in the case of injectable formulations. That is to say, a significant improvement in the pharmacokinetic parameters, e.g., the area under the curve (AUC), for a high molecular weight PEG insulin (relative to native), can more than compensate for its diminished activity.

In terms of the number of subunits, PEGs for use in the invention will typically comprise a number of $(OCH_2CH_2)$ subunits falling within one or more of the following ranges: 2 to about 900 subunits, from about 4 to about 200 subunits, from about 4 to about 170 subunits, from about 4 to about 140 subunits, from about 4 to about 100 subunits, from about 10 to about 100 subunits, from about 4 to about 70 subunits, from about 4 to about 45 subunits, and from about 4 to about 25 subunits.

A PEG-insulin conjugate of the invention may be mono-substituted (i.e., that is to say, having a PEG attached to a single reactive insulin site) di-substituted (having PEG moieties attached to two reactive sites, tri-substituted, or even have polymer attachments at more than 3 sites on the insulin molecule. Mono-substituted, di-substituted, and tri-substituted insulin are also referred to herein as PEG monomer, dimer, and trimer, respectively. Multi-substituted insulin (meaning insulin having PEG moieties covalently attached at 2 or more insulin sites) will typically although not necessarily possess the same PEG moiety attached to each reactive site. That is to say, PEG-insulin compositions having more than one type of PEG moiety attached to insulin are contemplated. Preferred compositions in accordance with the invention are those containing predominantly monomer and/or dimer insulin conjugates. Surprisingly, PEG-insulin compositions that are not site-specific (comprising a mixture of PEG-insulin species having PEG covalently coupled to more than one reactive site) have been found to possess pharmacokinetic and pharmacodynamic properties improved over native insulin, in particular, when administered to the lung (Example 11).

With respect to the position of PEG-substitution, the insulin molecule possesses several sites suitable for pegylation, with amino sites generally but not necessarily being most preferred. Specific insulin amino groups suitable for pegylation include the two N-termini, GlyA1 and PheB 1, as well as LysB29. These sites on the insulin molecule are also referred to herein simply as A1, B 1 and B29, respectively. Electrophilically activated PEGs for use in coupling to reactive amino groups on insulin include mPEG2-ALD, mPEG-succinimidyl propionate, mPEG-succinimidyl butanoate, mPEG-CM-HBA-NHA, mPEG-benzotriazole carbonate, mPEG-acetaldehyde diethyl acetal, and the like (Shearwater Corporation, Huntsville, Ala.).

A composition of the invention may, in one embodiment, contain predominantly (greater than 90%) monosubstituted insulin, e.g., mono-A1 insulin, mono-B1 insulin, or mono-B29 insulin. Such compositions may contain: i) mono-A1 insulin, ii) a mixture of mono-A1 insulin and mono-B1 insulin, or iii) a mixture of mono-A1, mono-B1 and mono-B29 insulin. Alternatively, a composition of the invention may contain predominantly di-substituted insulin, e.g., di-A1,B1-insulin, or di-A1,B29-insulin, or di-B1, B29-insulin, or any of the various combinations thereof.

Alternatively, a composition in accordance with the invention may contain a mixture of various PEG-insulin conjugates (i.e., PEG attached to any one of a combination of possible attachment sites). Using the amino sites on insulin as an example, a composition of the invention may contain any one or more of the following PEG-insulin conjugates: monoA1-PEG insulin, mono-B1-insulin, mono-B-29 insulin, di-A1, B1-insulin, di-A1,B29-insulin, di-B1, B29-insulin, or tri-A1,B-1,B29-insulin. In one embodiment, preferred are compositions containing predominantly monomers and dimers. Representative compositions may comprise PEG-insulin conjugates mixtures containing at least about 75% combined monomer and dimer, at least about 80% combined monomer and dimer, or at least about 85 to 90% combined monomer and dimer (e.g., Examples 5 and 6).

PheB 1 is a particularly preferred site for chemical modification by attachment of PEG. In particular, a PEG-insulin conjugate composition for use in the present invention may also be characterized in one embodiment as a composition in which at least about 70% of the B-1 sites on insulin are covalently coupled to PEG, regardless of the overall number of PEG-insulin species in the composition (e.g., Table 3A, Example 5). Alternative embodiments include those in which at least about 75% of the B-1 sites on insulin are covalently coupled to PEG, or in which at least about 80% of the B-1 sites on insulin are covalently coupled to PEG, or in which at least about 90% or the B-1 sites on insulin are covalently coupled to PEG.

Surprisingly, the inventors have discovered that random mixtures of PEG-insulin (prepared by random rather than site-directed pegylation), when administered to the lung, result in elevated blood levels of insulin that are sustained for at least 6 hours, and more typically for at least 8 hours or greater post-administration. Such mixtures are advantageous not only due to their beneficial pharmacokinetic and pharmacodynamic properties, but because their synthesis is much simpler (does not require multiple synthetic steps, does not require the use of protecting groups, does not require multiple purifications, etc.) than the corresponding site-specific approach.

Alternative sites in the native insulin molecule that can be chemically modified by covalent attachment of PEG include the 2 C-termini, Arg22B, His10B, His5A, Glu4A, Glu17A, Glu13B, and Glu21B.

In addition to native insulin, non-native insulins having one or more amino acid substitutions, insertions, or deletions may be utilized such that additional sites become available for chemical modification by attachment of one or more PEG moieties. This embodiment of the invention is particularly useful for introducing additional, customized pegylation-sites within the insulin molecule, for example, for forming a PEG-insulin having improved resistance to enzymatic degradation. Such an approach provides greater flexibility in the design of an optimized insulin conjugate having the desired balance of activity, stability, solubility, and pharmacological properties. Although mutations can be carried out, i.e., by site specific mutagenesis, at any number of positions within the insulin molecule, preferred is an insulin variant in which any one of the first four amino acids in the B-chain is replaced with a cysteine residue. Such cysteine residues can then be reacted with an activated PEG that is specific for reaction with thiol groups, e.g., an N-maleimidyl polymer or other derivative, as described in U.S. Pat. No. 5,739,208 and in International Patent Publication No. WO 01/62827. Exemplary sulfhydryl-selective PEGs for use in this particular embodiment of the invention include mPEG-forked maleimide (mPEG(MAL)$_2$), mPEG2-forked maleimide (mPEG2(MAL)$_2$), mPEG-maleimide (mPEG-MAL), and mPEG2-maleimide (mPEG2-MAL) (Shearwater Corporation). The structures of these activated PEGS are as follows: mPEG-CONHCH [CH$_2$CONH (CH$_2$CH$_2$O)$_2$CH$_2$CH$_2$-MAL, mPEG2-lysine-NH—CH [CH$_2$CONH (CH$_2$CH$_2$O)$_2$CH$_2$CH$_2$-MAL]$_2$, mPEG-MAL, and mPEG2-lysine-NH—CH $_2$CH$_2$NHC(O)CH$_2$CH$_2$MAL, respectively.

Additional mutations to the native insulin sequence may be employed, if necessary, to increase the bioactivity of a PEG-insulin conjugate whose biological activity is somewhat compromised as a result of pegylation. One such mutation is Thr8 to a His8. Additional mutations may be found, for example, in *Diabetes Care*, 13 (9), (1990), the content of which is herein incorporated by reference.

PEGs for use in the present invention may possess a variety of structures: linear, forked, branched, dumbbell, and the like. Typically, PEG is activated with a suitable activating group appropriate for coupling a desired site or sites on the insulin molecule. An activated PEG will possess a reactive group at a terminus for reaction with insulin. The term "linker" as used herein is meant to encompass an activating group positioned at a PEG terminus for reaction with insulin, and may further include additional (typically inert) atoms positioned between the PEG portion of the polymer and the activated group at the terminus, for ease in preparing the activated PEG. The linkers may contain any of a number of atoms, however, preferred are linkers containing methylenes intervening between the PEG backbone and the terminal activating group, e.g., as in mPEG-succinimidyl propionate and mPEG-butanoate. Representative activated PEG derivatives and methods for conjugating these agents to a drug such as insulin are known in the art and further described in Zalipsky, S., et al., *"Use of Functionalized Poly(Ethylene Glycols) for Modification of Polypeptides"* in Polyethylene Glycol Chemistry: Biotechnical and Biomedical Applications, J. M. Harris, Plenum Press, New York (1992), and in Advanced Drug Reviews, 16:157–182 (1995).

In one particular embodiment of the invention, the PEG portion of the conjugate is absent one or more lipophilic groups effective to significantly modify the water-soluble nature of the polymer or of the polymer-insulin conjugate. That is to say, the polymer or non-insulin portion of a conjugate of the invention may contain a group of atoms considered to be more lipophilic than hydrophilic (e.g., a carbon chain having from about 2 to 8–12 carbon atoms), however, if the presence of such a group or groups is not effective to significantly alter the hydrophilic nature of the polymer or of the conjugate, then such a moiety may be contained in the conjugates of the invention. That is to say, an insulin conjugate of the invention itself is characterized as hydrophilic, rather than lipophilic or amphiphilic. Typically, the polymer portion of an insulin conjugate, prior to coupling to insulin, whether or not containing such a lipid-loving group, will possess a high hydrophilic/lipophilic balance (HLB) number. The HLB number is based upon a weight percentage of each type of group (hydrophilic or lipophilic) in a molecule; values typically range from about 1–40. A polymer for use in the conjugates of the invention is, on a whole, characterized as hydrophilic, regardless of the presence of one or more lipid-loving substituents. In one embodiment of the invention, the polymer portion of a polymer-insulin conjugate is characterized by an HLB number of greater than 25 and more preferably greater than 30, or even more preferably greater than 35. In certain embodiments of the invention where such a lipophilic moiety may be present, the moiety is preferably not positioned at a terminus of a PEG chain.

Branched PEGs for use in the conjugates of the invention include those described in International Patent Publication WO 96/21469, the contents of which is expressly incorporated herein by reference in its entirety. Generally, branched PEGs can be represented by the formula R(PEG-OH)$_n$, where R represents the central "core" molecule and $_n$ represents the number of arms. Branched PEGs have a central core from which extend 2 or more "PEG" arms. In a branched configuration, the branched polymer core possesses a single reactive site for attachment to insulin. Branched PEGs for use in the present invention will typically comprise fewer than 4 PEG arms, and more preferably, will comprise fewer than 3 PEG arms. Branched PEGs offer the advantage of having a single reactive site, coupled with a larger, more dense polymer cloud than their linear PEG counterparts. One particular type of branched PEG can be represented as $(\text{MeO-PEG-})_p\text{R—X}$, where p equals 2 or 3, R is a central core structure such as lysine or glycerol having 2 or 3 PEG arms attached thereto, and X represents any suitable functional group that is or that can be activated for coupling to insulin. One particularly preferred branched PEG is mPEG2-NHS (Shearwater Corporation, Alabama) having the structure mPEG2-lysine-succinimide.

In yet another branched architecture, "pendant PEG" has reactive groups for protein coupling positioned along the PEG backbone rather than at the end of PEG chains as in the previous example. The reactive groups extending from the PEG backbone for coupling to insulin may be the same or different. Pendant PEG structures may be useful but are generally less preferred, particularly for compositions for inhalation.

Alternatively, the PEG-portion of a PEG-insulin conjugate may possess a forked structure having a branched moiety at one end of the polymer chain and two free reactive groups (or any multiple of 2) linked to the branched moiety for attachment to insulin. Exemplary forked PEGs are described in International Patent Publication No. WO 99/45964, the content of which is expressly incorporated herein by reference. The forked polyethylene glycol may optionally include an alkyl or "R" group at the opposing end of the polymer chain. More specifically, a forked PEG-insulin conjugate in accordance with the invention has the formula: $\text{R-PEG-L(Y-insulin)}_n$, where R is alkyl, L is a hydrolytically stable branch point and Y is a linking group that provides chemical linkage of the forked polymer to insulin, and n is a multiple of 2. L may represent a single "core" group, such as "—CH—", or may comprise a longer chain of atoms. Exemplary L groups include lysine, glycerol, pentaerythritol, or sorbitol. Typically, the particular branch atom within the branching moiety is carbon.

In one particular embodiment of the invention, the linkage of the forked PEG to the insulin molecule, (Y), is hydrolytically stable. In a preferred embodiment, n is 2. Suitable Y moieties, prior to conjugation with a reactive site on insulin, include but are not limited to active esters, active carbonates, aldehydes, isocyanates, isothiocyanates, epoxides, alcohols, maleimides, vinylsulfones, hydrazides, dithiopyridines, and iodacetamides. Selection of a suitable activating group will depend upon the intended site of attachment on the insulin molecule and can be readily determined by one of skill in the art. The corresponding Y group in the resulting PEG-insulin conjugate is that which results from reaction of the activated forked polymer with a suitable reactive site on insulin. The specific identity of such the final linkage will be apparent to one skilled in the art. For example, if the reactive forked PEG contains an activated ester, such as a succinimide or maleimide ester, conjugation via an amine site on insulin will result in formation of the corresponding amide linkage. These particular forked polymers are particularly attractive since they provide conjugates having a molar ratio of insulin to PEG of 2:1 or greater. Such conjugates may be less likely to block the insulin receptor site, while still providing the flexibility in design to protect the insulin against enzymatic degradation, e.g., by insulin degrading enzyme.

In a related embodiment, a forked PEG-insulin conjugate of the invention is represented by the formula: $\text{R-[PEG-L (Y-insulin)}_2]_n$. In this instance R represents a central core structure having attached thereto at least one PEG-di-insulin conjugate. Specifically, preferred forked polymers in accordance with this aspect of the invention are those were n is selected from the group consisting of 1,2,3,4,5, and 6. Exemplary core R structures may also be derived from lysine, glycerol, pentaerythritol, or sorbitol.

In an alternative embodiment, in any of the representative structures provided herein, the chemical linkage between insulin and the polymer branch point may be degradable (i.e., hydrolytically unstable). Alternatively, one or more degradable linkages may be contained in the polymer backbone to allow generation in vivo of a PEG-insulin conjugate having a smaller PEG chain than in the initially administered conjugate. Such optional features of the polymer conjugate may provide for additional control over the final desired pharmacological properties of the conjugate upon administration. For example, a large and relatively inert conjugate (i.e., having one or more high molecular weight PEG chains attached thereto, e.g., one or more PEG chains having a molecular weight greater than about 10,000, wherein the conjugate possesses essentially no bioactivity) may be administered, which then either in the lung or in the bloodstream, is hydrolyzed to generate a bioactive conjugate possessing a portion of the originally present PEG chain. In this way, the properties of the PEG-insulin conjugate may be somewhat more effectively tailored. For instance, absorption of the initial polymer conjugate may be slow upon initial administration, which is preferably but not necessarily by inhalation. Upon in-vivo cleavage of the hydrolytically degradable linkage, either free insulin (depending upon the position of the degradable linkage) or insulin having a small polyethylene tag attached thereto, is then released and more readily absorbed through the lung and/or circulated in the blood.

In one feature of this embodiment of the invention, the intact polymer-conjugate, prior to hydrolysis, is minimally degraded upon administration, such that hydrolysis of the cleavable bond is effective to govern the slow rate of release of active insulin into the bloodstream, as opposed to enzymatic degradation of insulin prior to its release into the systemic circulation.

Appropriate physiologically cleavable linkages include but are not limited to ester, carbonate ester, carbamate, sulfate, phosphate, acyloxyalkyl ether, acetal, and ketal. Such conjugates should possess a physiologically cleavable bond that is stable upon storage and upon administration. For instance, a PEG-cleavable linkage-insulin conjugate should maintain its integrity upon manufacturing of the final pharmaceutical composition, upon dissolution in an appropriate delivery vehicle, if employed, and upon administration irrespective of route.

More particularly, as described generally above, PEG-insulin conjugates having biodegradable linkages and useful in the present invention are represented by the following structures: PEG1-W-PEG2-insulin (where PEG1 and PEG2 can be the same or different) or PEG-W-insulin wherein W represents a weak, biodegradable linkage. These conjugates contain PEG arms or portions of PEG arms that are removable (i.e., cleavable) in-vivo. These particular modified insulins are typically substantially biologically inactive when intact, either due to the size of the intact PEG-portion of the molecule or due to steric blockage of the active sites on the insulin molecule by the PEG chain. However, such conjugates are cleaved under physiological conditions to thereby release insulin or a biologically active PEG-insulin capable of absorption into the systemic circulation, e.g., from the lung. In a first exemplary structure, the PEG1 portion may possess any of a number of different architectures discussed herein, and will typically possess a molecular weight of at least about 10,000, such that the conjugate is not rapidly absorbed upon administration. The PEG2 portion of the molecule preferably possesses a molecular weight of less than about 5000 daltons, more preferably less than 2000 daltons, and even more preferably less than 1000 daltons. Referring now to the secondary exemplary structure, PEG-W-insulin, the PEG portion will generally possess a molecular weight of at least about 10,000 Daltons or more.

In yet another specific embodiment of the invention, the PEG-insulin conjugate has a dumbbell-like structure in which two insulin moieties are interconnected by a central PEG. More specifically, such conjugates may be represented by the structure insulin-Y-PEG-Z-insulin, where Y and Z are hyrolytically stable linking groups linking insulin to the PEG moiety. In a particular embodiment, Z is an activated sulfone, which prior to conjugation, is suitable for reaction with thiol groups on insulin (e.g., cysteines). Alternatively, Y and Z may be any group suitable for covalent coupling with insulin. Additional examples are provided in U.S. Pat. No. 5,900,461, the content of which is expressly incorporated herein by reference.

Additional representative mono-and di-functional PEGs having either linear or branched structures for use in preparing the conjugates of the invention may be purchased from Shearwater Corporation (Alabama). Illustrative structures are described in Shearwater's 2001 catalogue entitled "Polyethylene Glycol and Derivatives for Biomedical Applications", the contents of which is expressly incorporated herein by reference.

B. Preparation

The reaction conditions for coupling PEG to insulin will vary depending upon the particular PEG derivative employed, the site of attachment on insulin and the particular type of reactive group (i.e., lysine versus cysteine), the desired degree of pegylation, and the like, and can readily be determined by one skilled in the art.

As exemplified in greater detail below, synthesis of the conjugates of the invention may be site-directed (Examples 1, 2 and 4) or may be random (Example 3). Suitable PEG activating groups for reaction with insulin amine groups (e.g., GlyA1, PheB1, Lys29B), are tresylate, aldehyde, epoxide, carbonylimidazole, active carbonates (e.g. succinimidyl carbonate), acetal, and active esters such as N-hydroxylsuccinimide (NHS) and NHS-derivatized PEGs. Of these, the most reactive are PEG carboxymethyl-NHS, norleucine-NHS, and succinimidyl carbonate. Additional PEG reagents for coupling to insulin include PEG succinimidyl succinate and propionate. PEG active esters suitable for use in the invention, e.g., having a single propanoic or butanoic acid moiety, are described in U.S. Pat. No. 5,672,662, the contents of which is incorporated herein in its entirety. Specific active esters for use in preparing the conjugates of the invention include mPEG-succinimidyl propionate and mPEG-succinimidyl butanoate (Examples 1–4).

Optimized experimental conditions for a specific conjugate can readily be determined, typically by routine experimentation, by one skilled in the art.

Reactive groups suitable for activating a PEG-polymer for attachment to a thiol (sulfhydryl) group on insulin include vinylsulfones, iodoacetamide, maleimide, and dithio-orthopyridine. Particularly preferred reagents include PEG vinylsulfones and PEG-maleimide. Additional representative vinylsulfones for use in the present invention are described in U.S. Pat. No. 5,739,208, the content of which is expressly incorporated herein by reference.

In some instances, the compositions of the invention comprise selectively PEGylated insulin, i.e., the resulting conjugates are essentially homogeneous with respect to the position and degree of pegylation. That is to say, site selective or site directed pegylation of an amino group will result in an insulin conjugate composition wherein primarily the intended target position, e.g., PheB1, has a PEG moiety attached thereto. Depending upon the intended site of pegylation, a protection/deprotection synthetic strategy may be necessary to prevent pegylation of non-target reactive sites within the insulin molecule, e.g., by employing a protecting group such as t-BOC (tert-butoxycarbonyl) or di-BOC (di- butoxycarbonyl). Other suitable amino protecting groups include carbobenzoxy (CBZ), trityl derivatives such as trityl (Tr), dimethoxytrityl (DMTr) and the like. Other protecting groups, such as cyclic diacyl groups or nitrophenylsulfenyl (Nps) may also prove useful for protecting amino functions. An exemplary site-directed synthesis of a 5K-PEG-insulin composition is provided in Examples 1 and 2.

Such site directed coupling chemistry employed to provide the insulin conjugates of the invention results in compositions having a large degree of substitution at a particular reactive site on the insulin molecule. These compositions can then, if desired, be further purified to provide compositions of essentially pure mono- or di-functional PEG-insulins.

An essentially pure PEG-insulin composition refers to one comprising a PEG-insulin conjugate that is at least about 90% pure, and preferably at least about 95% pure by any one of the following analytical methods. In this respect, purity refers to PEG-insulin conjugate content. That is to say, a PEG-insulin conjugate that is at least about 90% pure contains at least about 90% by weight of PEG-insulin conjugate species, while the other nearly 10% represents impurities that are not PEG-insulin conjugate. PEG-insulin conjugates of the invention are typically purified using one or more purification techniques such as ion exchange chromatography, size exclusion chromatography, affinity chromatography, hydrophobic interaction chromatography, and reverse phase chromatography. The overall homogeneity of the resulting PEG-insulin (number of insulin-PEG forms present) can be assessed using one or more of the following methods: chromatography, electrophoresis, mass spectrometry, and in particular, MALDI-MS, and NMR spectroscopy. One particularly useful method for identifying the sites of insulin modification is RP-HPLC peptide mapping, coupled with a USP identity test for human insulin using endoproteinase Glu-C (Example 6).

C. Characteristics of PEG-insulin Conjugates

In accordance with one aspect of the invention, provided are PEG-insulin conjugate compositions that are suitable for pulmonary administration. As can be seen by the in-vivo data in Examples 7–11, the PEG insulin conjugates of the invention, when administered to the lung, possess pharmacokinetic and pharmodynamic properties improved over native insulin. It has been shown that insulin can be modified with PEGs having a molecular weight of up to 5,000K to 10,000 K or greater, and still maintain activity. Activity of a representative PEG-insulin conjugate, 5K-PEG-insulin, is demonstrated in Example 7. Additionally, as can be seen from the examples provided herein, exemplary PEG-insulin conjugates possessing PEG chains with average molecular weights ranging from 750 daltons, to 2,000 daltons, to 5,000 daltons, when administered both intravenously and to the lung, are bioactive, are not substantially held up within the lung when administered to the lung, as evidenced by detectable serum levels of insulin, and are effective in producing a substantial suppression of glucose (Examples 7 to 11), which, in certain cases, is over a duration of time significantly greater than that observed for native insulin. Moreover, provided herein are PEG-insulin conjugates, which when administered to the lung, exhibit a rapid onset of action (within 1 hour of administration). A summary of pharmacokinetic and pharmacodynamic parameters for exemplary PEG-insulin compositions of the invention is provided in Table 13.

In general, a PEG-insulin composition of the invention will possess one or more of the following characteristics. The PEG-insulin conjugates of the invention maintain at least a measurable degree of specific activity. That is to say, a PEG-insulin conjugate in accordance with the invention will possesses anywhere from about 2% to about 100% or more of the specific activity of native insulin. In one preferred embodiment of the invention, the PEG-insulin conjugate will possess at least 10% or more of the biological activity of unmodified, native insulin and is substantially non-immunogenic. Preferably, the bioactivity of a conjugate of the invention will range from about 5% to at least about 20% or more of the bioactivity of native insulin. The bioactivity of a conjugate of the invention may be characterized indirectly, e.g., by monitoring blood glucose and insulin levels to generate the corresponding pharmacodynamic and/or pharmacokinetic data, or by RIA (radioimmunoassay).

In considering serum concentrations of insulin following administration of a PEG-insulin conjugate, e.g., to the lung, the conjugates described herein will typically peak (i.e., reach Cmax or the highest point in the concentration curve) at from around 2 to 8 hours post dose, and more typically will peak at around 3 to 6 hours or so. Moreover, the chemically modified insulins of the invention, and in particular, the prolonged effect insulin formulations provided herein, are effective in providing both a measurable glucose-lowering effect and sustained concentrations of insulin over a longer period of time than native insulin. More specifically, a PEG-insulin conjugate when administered to the lung will exhibit elevated levels of insulin (elevated over basal or baseline levels) for at least about 6 hours and preferably for at least 8 hours post administration. Preferably, a PEG-insulin conjugate when administered to the lung, results in elevated blood levels of insulin over a prolonged period of at least 9 hours, 10 hours, 12 hours or at least 14 hours post administration wherein above-basal levels of insulin conjugate are detectable in the bloodstream for such an extended duration post dose. Representative compositions demonstrating these features are provided in the Examples.

As described previously, an insulin conjugate of the invention is effective to lower blood glucose levels. Turning now to the ability of the compositions of the invention to suppress blood glucose, a PEG insulin conjugate when administered, e.g., to the lung, is effective to suppress blood glucose levels below basal levels for at least 6 hours post-administration. More particularly, a PEG-insulin composition of the invention is effective to suppress blood glucose levels below baseline for at least 8 hours, preferably for at least 10 hours, or more preferably for at least 12 hours or more post administration.

Moreover, the PEG-insulin formulations of the invention exhibit absolute pulmonary bioavailabilities that are improved over native insulin. Specifically, a PEG-insulin formulation as provided herein possesses an absolute pulmonary bioavailability that is at least about 1.2 times that of native insulin, preferably at least about 1.5 times that of native insulin, more preferably is at least about 2 times greater or even more preferably is at least about 2.5 or 3 times greater than that of native insulin. (Illustrative results are provided in Table 13).

III. Formulations

The polymer-insulin conjugate compositions of the invention may be administered neat or in therapeutic/pharmaceutical compositions containing additional excipients, solvents, stabilizers, etc., depending upon the particular mode of admistration and dosage form. The present conjugates may be administered parenterally as well as non-parenterally. Specific administration routes include oral, rectal, buccal, topical, nasal, ophthalmic, subcutaneous, intramuscular, intravenous, transdermal, and pulmonary. Most preferred are parenteral and pulmonary routes.

Pharmaceutical formulations for mammalian and preferably human administration will typically comprise at least one PEG-insulin conjugate of the invention together with one or more pharmaceutically acceptable carriers, as will be described in greater detail below, particularly for pulmonary compositions. Formulations of the present invention, e.g., for parenteral administration, are most typically liquid solutions or suspensions, while inhaleable formulations for pulmonary administration are generally liquids or powders, with powder formulations being generally preferred. Additional albeit less preferred compositions of the chemically modified insulins of the invention include syrups, creams, ointments, tablets, and the like.

Formulations and corresponding doses of insulin will vary with the concentration bioactivity of the insulin employed. Injectable insulin is measured in USP Insulin Units and USP Insulin Human Units (U); one unit of insulin is equal to the amount required to reduce the concentration of blood glucose in a fasting rabbit to 45 mg/dl (2.5 mM). Typical concentrations of insulin preparations for injection range from 30–100 Units/mL which is about 3.6 mg of insulin per mL. The amount of insulin required to achieve the desired physiological effect in a patient will vary not only with the particulars of the patient and his disease (e.g., type I vs. type II diabetes) but also with the strength and particular type of insulin used. For instance, dosage ranges for regular insulin (rapid acting) are from about 2 to 0.3 U insulin per kilogram of body weight per day. Compositions of the invention are, in one aspect, effective to achieve in patients undergoing therapy a fasting blood glucose concentration between about 90 and 140 mg/dl and a postprandial value below about 250 mg/dl. Precise dosages can be determined by one skilled in the art when coupled with the pharmacodynamics and pharmacokinetics of the precise insulin-conjugate employed for a particular route of administration, and can readily be adjusted in response to periodic glucose monitoring.

Individual dosages (on a per inhalation basis) for inhaleable insulin-conjugate formulations are typically in the range of from about 0.5 mg to 15 mg insulin-conjugate, where the desired overall dosage is typically achieved in from about 1–10 breaths, and preferably in from about 1 to 4 breaths. On average, the overall dose of PEG-insulin administered by inhalation per dosing session will range from about 10U to about 400U, with each individual dosage or unit dosage form (corresponding to a single inhalation) containing from about 5U to 400U.

A. Inhaleable Formulations of Chemically Modified Insulin

As stated above, one preferred route of administration for the insulin conjugates of the invention is by inhalation to the lung. Particular formulation components, characteristics and delivery devices will now be more fully described.

The amount of insulin conjugate in the formulation will be that amount necessary to deliver a therapeutically effective amount of insulin per unit dose to achieve at least one of the therapeutic effects of native insulin, i.e., the ability to control blood glucose levels to near normoglycemia. In practice, this will vary widely depending upon the particular insulin conjugate, its activity, the severity of the diabetic condition to be treated, the patient population, the stability of the formulation, and the like. The composition will generally contain anywhere from about 1% by weight to about 99% by weight PEG-insulin, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of PEG-insulin: 10%, 20%, 30%, 40%, 50%, 60%, 70%, 80%, 90% or more by weight. Preferably, powder compositions will contain at least about 60%, e.g., from about 60–100% by weight PEG-insulin. It is to be understood that more than one insulin may be incorporated into the formulations described herein and that the use of the term "agent" or "insulin" in no way excludes the use of two or more insulins or a combination of insulin with another active agent. (For example, an illustrative PEG-insulin formulation may also comprise native insulin).

A.1. Excipients

Compositions of the invention will, in most instances, include one or more excipients. Preferred are carbohydrate excipients, either alone or in combination with other excipients or additives. Representative carbohydrates for use in the compositions of the invention include sugars, derivatized sugars such as alditols, aldonic acids, esterified sugars, and sugar polymers. Exemplary carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like. Preferred are non-reducing sugars, sugars that can form a substantially dry amorphous or glassy phase when combined with an insulin conjugate, and sugars possessing relatively high Tgs (e.g., Tgs greater than 40° C., preferably greater than 50° C., more preferably greater than 60° C., and even more preferably greater than 70° C., and most preferably having Tgs of 80° C. and above).

Additional excipients include amino acids, peptides and particularly oligomers comprising 2–9 amino acids, and more preferably 2–5 mers, and polypeptides, all of which may be homo or hetero species. Representative amino acids include glycine (gly), alanine (ala), valine (val), leucine (leu), isoleucine (ile), methionine (met), proline (pro), phenylalanine (phe), trytophan (trp), serine (ser), threonine (thr), cysteine (cys), tyrosine (tyr), asparagine (asp), glutamic acid (glu), lysine (lys), arginine (arg), histidine (his), norleucine (nor), and modified forms thereof. One particularly preferred amino acid is leucine.

Also preferred for use as excipients in inhaleable compositions are di- and tripeptides containing two or more leucyl residues, as described in Inhale Therapeutic System's International patent application PCT/US00/09785, incorporated herein by reference in its entirety.

Also preferred are di- and tripeptides having a glass transition temperature greater than about 40° C., more preferably greater than 50° C., even more preferably greater than 60° C., and most preferably greater than 70° C.

Although less preferred due to their limited solubility in water, additional stability and aerosol performance-enhancing peptides for use in the invention are 4-mers and 5-mers containing any combination of amino acids as described above. More preferably, the 4-mer or 5-mer will comprise two or more leucine residues. The leucine residues may occupy any position within the peptide, while the remaining (i.e., non-leucyl) amino acids positions are occupied by any amino acid as described above, provided that the resulting 4-mer or 5-mer has a solubility in water of at least about 1 mg/ml. Preferably, the non-leucyl amino acids in a 4-mer or 5-mer are hydrophilic amino acids such as lysine, to thereby increase the solubility of the peptide in water.

Polyamino acids, and in particular, those comprising any of the herein described amino acids, are also suitable for use as stabilizers. Preferred are polyamino acids such as polylysine, poly-glutamic acid, and poly(lys, ala).

Additional excipients and additives useful in the present compositions and methods include but are not limited to proteins, non-biological polymers, and biological polymers, which may be present singly or in combination. Suitable excipients are those provided in Inhale Therapeutic Systems' International Publication Nos. WO 96/32096 and 98/16205. Preferred are excipients having glass transition temperatures (Tg), above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. The compositions may also include a buffer or a pH adjusting agent, typically but not necessarily a salt prepared from an organic acid or base. Representative buffers include organic acid salts of citric acid, ascorbic acid, gluconic acid, carbonic acid, tartaric acid, succinic acid, acetic acid, or phthalic acid. Other suitable buffers include Tris, tromethamine hydrochloride, borate, glycerol phosphate and phosphate. Amino acids such as glycine are also suitable.

The compositions of the invention may also include additional polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin.

The compositions may further include flavoring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, although preferably not in liposomal form), fatty acids and fatty esters, steroids (e.g., cholesterol), and chelating agents (e.g., EDTA, zinc and other such suitable cations). The use of certain di-substituted phosphatidylcholines for producing perforated microstructures (i.e., hollow, porous microspheres) is described in greater detail below. Other pharmaceutical excipients and/or additives suitable for use in the compositions according to the invention are listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998).

In one embodiment, a composition in accordance with the invention may be absent penetration enhancers, which can cause irritation and are toxic at the high levels often necessary to provide substantial enhancement of absorption. Specific enhancers, which may be absent from the compositions of the invention, are the detergent-like enhancers such as deoxycholate, laureth-9, DDPC, glycocholate, and the fusidates. Certain enhancers, however, such as those that protect insulin from enzyme degradation, e.g., protease and peptidase inhibitors such as alpha-i antiprotease, captropril, thiorphan, and the HIV protease inhibitors, may, in certain embodiments of the invention, be incorporated in the PEG-insulin formulations of the invention. In yet another embodiment, the PEG-insulin conjugates of the invention may be absent liposomes, lipid matrices, and encapsulating agents.

Generally, the pharmaceutical compositions of the invention will contain from about 1% to about 99% by weight excipient, preferably from about 5%–98% by weight excipient, more preferably from about 15–95% by weight excipient. Even more preferably, the spray dried composition will contain from about 0–50% by weight excipient, more preferably from 0–40% by weight excipient. In general, a high insulin concentration is desired in the final pharmaceutical composition. Typically, the optimal amount of excipient/additive is determined experimentally, i.e., by preparing compositions containing varying amounts of excipients (ranging from low to high), examining the chemical and physical stability of the PEG-insulin, MMADs and dispersibilities of the pharmaceutical compositions, and then further exploring the range at which optimal aerosol performance is attained with no significant adverse effect upon insulin stability.

A.2. Preparing Dry Powders

Dry powder formulations of the invention comprising a PEG-insulin conjugate may be prepared by any of a number of drying techniques, and preferably by spray drying. Spray drying of the formulations is carried out, for example, as described generally in the "Spray Drying Handbook", 5$^{th}$ ed., K. Masters, John Wiley & Sons, Inc., NY, N.Y. (1991), and in Platz, R., et al., International Patent Publication Nos. WO 97/41833 (1997) and WO 96/32149 (1996), the contents of which are incorporated herein by reference.

Solutions of PEG-insulin conjugates are spray dried in a conventional spray drier, such as those available from commercial suppliers such as Niro A/S (Denmark), Buchi (Switzerland) and the like, resulting in a dispersible, dry powder. Optimal conditions for spray drying the PEG-insulin solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause degradation of the PEG-insulin in the sprayed material. Such temperatures are typically determined experimentally, although generally, the inlet temperature will range from about 50° C. to about 200° C., while the outlet temperature will range from about 30° C. to about 150° C. Preferred parameters include atomization pressures ranging from about 20–150 psi, and preferably from about 30–40 to 100 psi. Typically the atomization pressure employed will be one of the following (psi): 20, 30, 40, 50, 60, 70, 80, 90, 100, 110, 120 or above.

Respirable PEG-insulin compositions having the features described herein may also be produced by drying certain formulation components which result in formation of a perforated microstructure powder as described in WO 99/16419, the entire contents of which are incorporated by reference herein. The perforated microstructure powders typically comprise spray-dried, hollow microspheres having a relatively thin porous wall defining a large internal void. The perforated microstructure powders may be dispersed in a selected suspension media (such as a non-aqueous and/or fluorinated blowing agent) to provide stabilized dispersions prior to drying. The use of relatively low density perforated (or porous) microstructures or microparticulates significantly reduces attractive forces between the particles, thereby lowering the shear forces, increasing the flowability and dispersibility of the resulting powders, and reducing the degradation by flocculation, sedimentation or creaming of the stabilized dispersions thereof.

Alternatively, a PEG-insulin composition for pulmonary delivery may comprise aerodynamically light particles as described in U.S. Pat. No. 6,136,295.

A powdered formulation of the invention may also be prepared by lyophilization, vacuum drying, spray freeze drying, super critical fluid processing (e.g., as described in Hanna, et al., U.S. Pat. No. 6,063,138), air drying, or other forms of evaporative drying.

In yet another approach, dry powders may be prepared by agglomerating the powder components, sieving the materials to obtain agglomerates, spheronizing to provide a more spherical agglomerate, and sizing to obtain a uniformly-sized product, as described, e.g., and in Ahlneck, C., et al., International PCT Publication No. WO 95/09616, 1995, incorporated herein by reference.

Dry powders may also be prepared by blending, grinding, sieving or jet milling formulation components in dry powder form.

Once formed, the dry powder compositions are preferably maintained under dry (i.e., relatively low humidity) conditions during manufacture, processing, and storage. Irrespective of the drying process employed, the process will preferably result in inhaleable, highly dispersible particles comprising a chemically modified insulin as described herein.

A.3. Features of Dry Powder Formulations

Powders of the invention are further characterized by several features, most notably, one or more of the following: (i) consistently high dispersibilities, which are maintained, even upon storage (ii) small aerodynamic particles sizes (MMADs), (iii) improved fine particle dose values, i.e., powders having a higher percentage of particles sized less than 3.3 microns MMAD, all of which contribute to the improved ability of the powder to penetrate to the tissues of the lower respiratory tract (i.e., the alveoli) for delivery to the systemic circulation. These physical characteristics of the inhaleable powders of the invention, to be described more fully below, are important in maximizing the efficiency of aerosolized delivery of such powders to the deep lung.

Dry powders of the invention are composed of aerosolizable particles effective to penetrate into the lungs. The particles of the invention have a mass median diameter (MMD) of less than about 20–30 $\mu$m, or less than 20 $\mu$m, or less than about 10 $\mu$m, preferably less than about 7.5 $\mu$m, and more preferably less than about 4 $\mu$m, and even less than about 3.5 $\mu$m, and usually are in the range of 0.1 $\mu$m to 5 $\mu$m in diameter. Preferred powders are composed of particles having an MMD from about 0.2 to 4.0 $\mu$m. In some cases, the powder will also contain non-respirable carrier particles such as lactose, where the non-respirable particles are typically greater than about 40 microns in size.

The powders of the invention are further characterized by an aerosol particle size distribution less than about 10 μm mass median aerodynamic diameter (MMAD), preferably having MMADs less than about 5 μm, more preferably less than 4.0 μm, even more preferably less than 3.5 μm, and most preferably less than 3 μm. The mass median aerodynamic diameters of the powders will characteristically range from about 0.1–10 μm, preferably from about 0.2–5.0 μm MMAD, more preferably from about 1.0–4.0 μm MMAD, and even more preferably from about 1.5 to 3.0 μm. Small aerodynamic diameters can generally be achieved by a combination of optimized spray drying conditions and choice and concentration of excipients.

The PEG-insulin powders of the invention may further be characterized by their densities. A powdered composition for inhalation will generally possess a bulk density from about 0.1 to 10 g/cubic centimeter, preferably from about 0.1–2 g/cubic centimeter, and more preferably from about 0.15–1.5 g/cubic centimeter.

The powders will generally have a moisture content below about 20% by weight, usually below about 10% by weight, and preferably below about 5% by weight. Preferred powders in accordance with the invention having a moisture content that is below about one or more of the following weight percentages: 15%, 10%, 7%, 5%, or 3%. Such low moisture-containing solids tend to exhibit a greater stability upon packaging and storage.

Additionally, the spray drying methods and stabilizers described herein are effective to provide highly dispersible PEG-insulin formulations. For powder formulations, the emitted dose (ED) of these powders is typically greater than 30%, and usually greater than 40%. More preferably, the ED of the powders of the invention is greater than 50%, and is often greater than 60%.

The compositions described herein also possess good stability with respect to both chemical stability and physical stability, i.e., aerosol performance over time. Generally, with respect to chemical stability, the PEG-insulin conjugate contained in the formulation will degrade by no more than about 15% upon spray drying. That is to say, the powder will possess at least about 85% intact PEG-insulin conjugate, preferably at least about 90 or 95% intact conjugate, and even more preferably will contain at least about 97% or greater intact PEG-insulin. Preferably, the spray drying process will result in powders having less than about 10% total protein aggregates, that is to say, greater than 90% by weight of the chemically modified insulin being in monomeric form.

With respect to aerosol performance, compositions of the invention are generally characterized by a drop in emitted dose of no more than about 20%, preferably no more than about 15%, and more preferably by no more than about 10%, when stored under ambient conditions for a period of three months.

A.4. Administration of the Composition

PEG-insulin formulations as described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135, Oct. 17, 1995; Smith, A. E., et al., U.S. Pat. No. 5,740,794, Apr. 21, 1998; and in Smith, A. E., et. al., U.S. Pat. No. 5,785,049, Jul. 28, 1998, herein incorporated by reference. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in Parks, D. J., et al., International Patent Publication WO 97/41031, Nov. 6, 1997, incorporated herein by reference.

Other dry powder dispersion devices for pulmonary administration of dry powders include those described, for example, in Newell, R. E., et al, European Patent No. EP 129985, Sep. 7, 1988; in Hodson, P. D., et al., European Patent No. EP472598, Jul. 3, 1996; in Cocozza, S., et al., European Patent No. EP 467172, Apr. 6, 1994, and in Lloyd, L. J. et al., U.S. Pat. No. 5,522,385, Jun. 4, 1996, incorporated herein by reference. Also suitable for delivering PEG-insulin dry powders are inhalation devices such as the Astra-Draco "TURBUHALER". This type of device is described in detail in Virtanen, R., U.S. Pat. No. 4,668,218, May 26, 1987; in Wetterlin, K., et al., U.S. Pat. No. 4,667,668, May 26, 1987; and in Wetterlin, K., et al., U.S. Pat. No. 4,805,811, Feb. 21, 1989, all of which are incorporated herein by reference. Other suitable devices include dry powder inhalers such as Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572, Sep. 30, 1997, incorporated herein by reference.

An inhaleable PEG-insulin composition may also be delivered using a pressurized, metered dose inhaler (MDI), e.g., the Ventolin® metered dose inhaler, containing a solution or suspension of drug in a pharmaceutically inert liquid propellant, e.g., a chlorofluorocarbon or fluorocarbon, as described in Laube, et al., U.S. Pat. No. 5,320,094, Jun. 14, 1994, and in Rubsamen, R. M., et al, U.S. Pat. No. 5,672,581 (1994), both incorporated herein by reference.

Alternatively, the PEG-insulins described herein may be dissolved or suspended in a solvent, e.g., water or saline, and administered by nebulization. Nebulizers for delivering an aerosolized solution include the AERx™ (Aradigm), the Ultravent® (Mallinkrodt), the Pari LC Plus™ or the Pari LC Star™ (Pari GmbH, Germany), the DeVilbiss Pulmo-Aide, and the Acorn II® (Marquest Medical Products).

As previously described, the PEG-insulin conjugates described herein can also be administered parenterally by intravenous injection, or less preferably by intramuscular or by subcutaneous injection. Precise components of such formulations can be readily determined by one skilled in the art. Suitable formulation types for parenteral administration include ready-for-injection solutions, dry powders for combination with a solvent prior to use, suspensions ready for injection, dry insoluble compositions for combination with a vehicle prior to use, emulsions and liquid concentrates for dilution prior to administration. For instance, an injectable solution of a PEG-insulin composition of the invention may include the composition dissolved in an aqueous vehicle such as aqueous sodium chloride, Ringers solution, a dextrose-injection solution, lactated Ringers solution and the like, and may include one or more pharmaceutically acceptable compatible excipients or additives as described above.

IV. Utility

The compositions of the invention are useful, when administered by any suitable route of administration, and preferably by inhalation or by injection, in a therapeutically effective amount to a mammalian subject, for treating diabetes mellitus, and in particular, type I or type II diabetes.

All articles, books, patents and other publications referenced herein are hereby incorporated by reference in their entirety.

The following examples illustrate, but in no way are intended to limit the scope of the present invention.

EXAMPLES

Materials and Methods

Polyethylene glycol reagents were obtained from Shearwater Corporation (Huntsville, Ala.).

Human insulin was obtained from Diosynth, Inc.

Example 1

Synthesis of Di-$N^{\alpha A1},N^{\epsilon B29}$-t-Boc-Insulin

A composition composed primarily of mono-pegylated insulin was prepared in a site-specific fashion as set forth in Examples 1 and 2 using an exemplary linear 5,000 Dalton polyethylene glycol.

Di-protected insulin was first prepared as follows. 602 mg of human insulin (0.103 mmol) was dissolved in 3.0 mL of anhydrous dimethyl sulfoxide (DMSO) containing 166 uL of triethylamine. 50□1 of di-tert-butyldicarbonate (0.215 mmol) was added to the insulin solution. After 60 min at room temperature, the reaction solution was poured into 240 mL of acetone followed by addition of 3 drops of 6 M HCl to initiate flocculation. The precipitate was isolated by filtration, and dried in vacuo. The reaction product was purified by preparative HPLC using a Waters 25×100 mm C18 column (mean particle size, 15 μm; pore size, 100A). Mixtures of acetonitrile and 0.1%TFA in deionized water were used as eluents at a rate of 3.0 mL/min. The product was collected, distilled to remove acetonitrile, and then lyophilized. Yield was 164.8 mg (26.7%, MW ~6000 by MALDI).

Example 2

Synthesis of Mono-Pegylated mPEG-5K-SPA-PheB1-Insulin Conjugate $N^{\alpha B1}$-Methoxypoly (ethylene glycol)5K-insulin (mPEG5K-PheB1-insulin)

150 mg (~0.025 mmol) of newly purified di-$N^{\alpha A1}$, $N^{\epsilon B29}$-t-boc-Insulin from Example 1 was dissolved in 4 mL of DMSO containing 95 μL of triethylamine. 169 mg (0.032 mmol) of mPEG-SPA-5000 (mPEG-succinimidyl propionate, mPEG-O-CH$_2$CH$_2$C(O)O-succinimide, MW 5,000) was added to the insulin solution. After incubation overnight (29 hours) at room temperature, the resulting mPEG-insulin derivative was diluted to 100 mL with D.I. water, dialyzed against D.I. water for 4 hours and then lyophilized. The lyophilized product was re-dissolved in 4 mL of anhydrous TFA and maintained under N$_2$ at 0° C. for 1.5 hours to remove the Boc protecting groups. The deprotected mPEG-insulin was diluted to 50 mL with D.I. water and dialyzed against 0.1% NH$_4$HCO$_3$ and D.I. water overnight. Lyophilization of the product yielded a white powder. Yield was 117.6 mg (41.6%, MW~11311.6 by MALDI).

The percentage of mono-conjugated insulin, based upon mass spectral data, was approximately 90%, confirming the site specific nature of this synthetic approach. Additional characterization data is provided in Example 5. Insulin content of the resulting product was 51.3%. For ease of reference, $N^{\alpha B1}$-Methoxypoly(ethylene glycol)5K-propionamido-insulin or mPEG5K-PheB1-insulin will be referred to herein as "5K PEG insulin".

Example 3

Synthesis of mPEG-2K-SPA-Insulin Conjugate

The following approach was utilized to prepare insulin pegylated in a non-site specific (i.e., random) fashion utilizing an exemplary linear polyethylene glycol having a molecular weight of approximately 2,000 Daltons. 0.1012 g of insulin (MW 5826 Da, 0.01737 mmol) was dissolved in 0.5 mL of anhydrous DMSO and treated with 50 μL of triethylamine (0.3587 mmol, 20 fold molar excess). To the above reaction mixture was added 52 mg of m-SPA-2000 (mPEG-succinimidyl propionate, Shearwater Corporation, MW~2000 Da, 0.02605 mmol, 1.5 fold molar excess). The mixture was stirred for about 17 hours at room temperature under nitrogen. The reaction mixture was then dissolved in 0.1% TFA to a total volume of 5.5 mL and purified by reverse phase IHPLC using a C-18 column, and acetonitrile/0.1%TFA as eluent). Reverse phase HPLC revealed a mixture of both mono (one PEG attached) and di-pegylated (two PEGs attached) product; the composition is referred to herein as "2K PEG insulin".

Yield: 68 mg

Insulin content by RP-HPLC: 50.5 mg

Example 4

Synthesis of mPEG-750 Da -SPA-Insulin Conjugate

A composition composed predominantly of insulin pegylated at the B1 site was prepared in a site-specific fashion using a representative polyethylene glycol modifier, i.e, a linear 750 Dalton polyethylene glycol having a succinimidyl propionate terminus suitable for covalent attachment to insulin.

4A. Synthesis of Di-$N^{A1},N^{B29}$-t-Boc-Insulin

Di-protected insulin was prepared as follows. 602 mg of human insulin (0.103 mmol) was dissolved in 3.0 mL of anhydrous dimethyl sulfoxide (DMSO) containing 166 uL of triethylamine. 50ul of di-tert-butyldicarbonate (0.215 mmol) was added to the insulin solution. After 60 min at room temperature, the reaction solution was poured into 240 mL of acetone followed by addition of 3 drops of 6 M HCl to initiate flocculation. The precipitate was isolated by filtration and dried in vacuo. The reaction product was purified by preparative HPLC using a Waters 25×100 mm C18 column (mean particle size, 15um; pore size, 100A). Mixtures of acetonitrile and 0.1%TFA in deionized water were used as eluents at a rate of 3.0 mL/min. The product was collected, distilled to remove acetonitrile, and then lyophilized. Yield was 164.8 mg (26.7%, MW~6000 by MALDI).

4B. Synthesis of mPEG-750 Da-SPA-PheB1-Insulin Conjugate 63.4 mg (~0.01056 mmol) of newly purified di-$N^{A1},N^{B29}$-t-boc-Insulin from Example 4A was dissolved in 0.5 mL of DMSO containing 200 uL of triethylamine. 33 mg (0.03173 mmol, MW of mSPA750 is about 1040Da) of mPEG-SPA-750 (mPEG-succinimidyl propionate, mPEG—O—CH2CH2C(O)O-succinimide, PEG MW 750) was added to the insulin solution. After incubation overnight (29 hours) at room temperature, 300 uL of TFA was added to the reaction mixture and the resulting mPEG-insulin derivative was precipitated in 100 mL ethyl ether and dried under vacuum.

Yield was about 28.5 mg with 21.3 mg of insulin content measured by reverse phase HPLC (33.6%, MW~6639.3Da by MALDI. For simplicity, the composition is referred to herein as "750 PEG Insulin".

Two different syntheses were carried out on this material both utilizing the above synthetic methodology with one exception: one synthesis was carried out at a molar ratio of mPEG-SPA-750 to insulin of 7:1 while the other synthesis was conducted at a molar ratio of mPEG-SPA-750 to insulin of 3:1. The product compositions resulting from these two preparations are referred to herein as "750-1 PEG insulin" (molar ratio of PEG reagent to insulin was 7:1) and "750-2 PEG insulin" (molar ratio of PEG reagent to insulin was 3:1).

Example 5

Characterization of Exemplary PEG-Insulin Compositions

The pegylated insulin conjugate compositions described above were further characterized by various analytical techniques.

Mass spectrometry was utilized to provide an estimate of the relative amounts of mono, di, and tri-conjugated insulin (also referred to as PEG insulin monomer, dimer, and trimer) present in each of the compositions based upon relative peak areas. The results are provided in Table 1 below.

TABLE 1

Relative Amounts of Mono, Di, and Tri-Conjugated Insulin Based on Mass Spectrometry

| PEG-Insulin Composition | % Monoconjugate | % Diconjugate | % Triconjugate |
|---|---|---|---|
| 5K PEG insulin | 91 | 4 | not determined |
| 750-1 PEG insulin | 46 | 39 | 15 |
| 750-2 PEG insulin | 60 | 32 | 8 |
| 2K PEG insulin | 51 | 45 | not determined |

Size exclusion chromatography (SEC) was carried out on the 750-1, 750–2 and 2K PEG-insulin compositions described above employing two Shodex SEC columns (part number KW-802.5) assembled in series on a Waters 2690 HPLC system. The mobile phase consisted of 22% glacial acetic acid and 33% acetonitrile (V/V) in water. The chromatography data was used as an alternative approach for determining the relative amounts of mono, di, and tri-conjugated insulin in each of these compositions. The results are presented in Table 2 below. As can be seen by a comparison of the data in Tables 1 and 2, the two different methods provide results that are in close agreement with respect to the relative amounts of each type of conjugate present in the compositions.

TABLE 2

Relative Amounts of Mono, Di, and Tri-Conjugated Insulin Based on HP-SEC

| Insulin Type | % Monoconjugate | % Diconjugate | % Triconjugate | % Other |
|---|---|---|---|---|
| PEG 750-1 | 48 | 47 | 5 | 0 |
| PEG 750-2 | 66 | 26 | 7 | 2 |
| PEG 2000 | 40 | 51 | nd | 9 |

Additional studies were carried out to determine the distribution of the various positional conjugates in each of three exemplary compositions, i.e., the extent of substitution at each of the three possible attachment sites, A-1Gly, B-1Phe or B-29 Lys. Dithiothreitol (DTT, Sigma) was used to reduce the disulfide bonds in the insulin samples, causing the covalent attachments between the insulin A and B chains to be broken.

To carry out the reduction reactions, the PEG-insulin samples were dissolved in 8 M urea containing 0.4 M ammonium bicarbonate at about 0.2 mg/mL of equivalent insulin mass for each conjugated species. DTT was dissolved in water (7 mg/ml) to form an aqueous DTT solution. One part of DTT solution was then added to 5 parts of each of the insulin solutions, and the reduction reaction was carried out at 50° C. for 15 minutes. The reduced 750 PEG insulin compositions were alkylated with iodoacetamide (Sigma). Six parts of the PEG-insulin solutions were reacted with 1 part of 100 mM iodoacetamide prior to chromatography and enzyme digestion. The reaction products were then analyzed by HPLC. Percent conjugation to either the A or B chain of insulin was estimated based upon the amount of insulin A or B chain that eluted later than the control (and attributed to conjugation to polyethylene glycol). These late-eluting peaks were therefore missing at the expected retention times for the control. Relative peak areas were used to provide an indication of the percent conjugation of polyethylene glycol to either the A or B chain of insulin.

To further explore the relative amount of PEG attached to B-29 Lys versus B1-Phe, the reduced and alkylated A and B chains of the 750-1 and 750-2 PEG insulin compositions from the DTT-reductions described above were further digested with the sequencing grade enzyme Endoproteinase Glu-C (Sigma). A solution containing the enzyme at 0.125 $\mu g/\mu L$ in aqueous ammonium bicarbonate was prepared. Prior to enzyme solution addition, the insulin concentration in each of the reduced reaction mixtures was 0.05 $\mu g/\mu L$ in 8 M urea containing 0.4 M ammonium bicarbonate. 1 part enzyme solution was then added to 40 parts insulin solution. Digestion with Endoproteinase Glu-C enzyme produces the insulin peptide fragments of A1-A4, A5-A17, A18-A21, B1-B13, B14-B21, AND B22-B30.

Fragments resulting from the enzymatic digests for both the A and B chains of the 750-1 and 750-2 PEG insulin compositions were analyzed by HPLC to estimate the overall distribution of PEG attachment sites to insulin for each of these compositions. The percent of the peak missing relative to the control provided an estimation of the amount of the fragment conjugated to PEG, since that fragment eluted elsewhere on the chromatogram.

TABLE 3A

Distribution of PEG Attachment Sites for Exemplary PEG-Insulin Formulations

| Insulin type | % of A1 Sites Conjugated | % of B-1 sites Conjugated | % of B-29 Sites Conjugated |
|---|---|---|---|
| PEG 750-1 | 30 | 95 | 21 |
| PEG 750-2 | 11 | 95 | 15 |
| PEG 2000 | 63 | 85* | |

*no digestion data, reduced recovery only

The numbers in Table 3A are based on the possibility of each site being 100 percent conjugated. For example, each mono-species has 3 possible configurations (mono-A1, mono-B1, mono-B-29) and each diconjugate has 3 configurations (di-A1, B-1; di-A-1,B-29; and di-B-1, B-29). Looking at the data in Table 3A, e.g., for PEG-750-1, over all of the possible species present in the composition, 95% of the PEG-insulin conjugates possess a polyethylene glycol covalently attached at the B-1 site.

TABLE 3B

Various Conjugate Species Possible

| Types | MONO-conjugate | | | DI-conjugate | | | TRI-conjugate | HMWP |
|---|---|---|---|---|---|---|---|---|
| Species # | 1 | 2 | 3 | 4 | 5 | 6 | 7 | 8 |
| Point of Conjugation | A-1 | B-1 | B-29 | (A-1 + B-1) | (A-1 + B-29) | (B-1 + B-29) | (A-1 + B-1 + B-29) | Conjugated Insulin Dimers |

Example 6

Comparison of the Rate of Enzymatic Digestion of 750-2 PEG Insulin Versus Unmodified Insulin The rate of enzymatic digestion of 750-2 PEG-insulin by chymotrypsin was compared to that of insulin.

An insulin control and a PEG 750 insulin-2 composition was prepared at 1 mg/mL in phosphate buffered saline solution at pH 7.8. Chymostrypsin was prepared at 1 mg/mL in 1 mM HCl solution. 1 part of the enzyme solution was added to 20 parts of the insulin solution. Small aliquots of the mixed solution were withdrawn approximately every hour.

A RP(reverse phase)-HPLC method was developed using a C-18 column with a mobile phase containing sodium perchlorate, phosphoric acid, and acetonitrile. An acetonitrile gradient was employed to elute the assortment of PEGylated insulin species in a group of slightly resolved peaks monitored at 214 nm. The group of peaks were integrated manually as one peak and labeled as PEG insulin. As the digestion proceeded, the loss of intact PEG insulin and insulin were plotted (FIG. 1). Their half-life in the presence of chymotrypsin was estimated.

The length of time required for enzymatic digestion of half of the concentration of the main component of the 750-2 PEG insulin composition was five times greater than for unmodified insulin. That is to say, it took five times longer for digestion by chymostrypsin of half the concentration of the illustrative pegylated insulin than for regular insulin. These results demonstrate the potential of PEG insulin conjugates for prolonged residence time in the alveoli due to enhanced resistance to proteolytic degradation when compared to unmodified insulin.

Example 7

Evaluation of Serum Glucose and Insulin Concentrations Following Intraveneous Administration of 5K PEG Insulin in Rats (P-2001-015)

This study was conducted to determine whether the activity of insulin in the 5K PEG insulin composition was retained upon chemical modification with an exemplary 5K polyethylene glycol chain, and to explore the dose and glucose response curves for these compositions when administered intraveneously.

Pre-cannulated (jugular/femoral vein [JVC/FVC]) male Sprague Dawley Rats (325–350 grams) having an access port threaded under the skin externalizing at the nape of the neck were supplied by Hilltop Lab Animals Inc. (P.O. Box 183, Scottdale, Pa. 15683). The jugular cannulas were filled with a solution (lumen filler) of pharmaceutical grade Polyviny-Pyrrolidone (PVP—MW 40,000), physiological saline and sodium heparin to retain patency. The nylon filament plug sealing the cannula was removed and replaced with a Monoject blunt cannula 23G×1 (VWR #53498-484) on the day of the study. The test system included 1 male rat randomly chosen for the placebo group, 2 male rats randomly chosen for the non-pegylated group, and 4 male rats randomly chosen for the PEG-insulin group. The source of pegylated insulin for this study was 5K PEG insulin from Example 2. Doses were administered intraveneously.

Number/Sex of Animals

Day 1: IM/Group for the placebo Group 1

2M/Group for Group 2; 4M/Group for Groups 3–5

The animals were fasted for 12–18 hours prior to the initiation of the study. Human insulin (Diosynth) was stored at −20° C. prior to use. 5K PEG Insulin (Example 2) was stored at −20° C. prior to use. Two different solutions for administration were prepared:

Solutions for I.V. Administration

Non-PEGylated Human Insulin (1.0 mg/ml Stock): 1.0 ml of PBS was added to 1.0 mg of insulin powder.

5K PEG Insulin: (1.0 mg/ml Human Insulin-concentration is based upon insulin rather than on the conjugate): 6.0 ml of PBS was added to 11.7 mg of 5K PEG Insulin powder.

The animals were anesthetized with inhaled isoflurane. The i.v. doses (300 μL/animal) were given through the FVC and then the catheter was tied off to eliminate cross contamination with the blood draws. All blood samples were drawn through the JVC. Phosphate buffered saline (PBS) was administered to Group 1 as a 300 μL i.v. dose. Non-pegylated human insulin was administered to Group 2 as a 20 μg/animal i.v. dose. The PEGylated human insulin formulation was administered to Group 3 as a 20 μg/animal i.v. dose, Group 4 as a 40 μg/animal i.v. dose, and Group 5 as a 30 μg/animal i.v. dose. Blood samples (~500 μL) were collected from the JVC at predose (2 to 0.25 hours prior to dosing), 10, 15, 30, 60, 120, and 180 minutes postdose. A small amount of blood was placed on a glucose test strip for determination of blood glucose by the Glucometer Elite glucose monitor (Bayer Corp., Elkart, Ind.). The remainder of the sample was placed into serum separator tubes and placed into the centrifuge to separate the blood. The serum was then decanted into a separate tube and analyzed by radioimmunoassay (RIA). Means and standard deviations (SD) were calculated using Microsoft® Excel 2000.

TABLE 4

Summary of In-Vivo Experiments
The following are the actual doses administered and
actual animal numbers per
group that were used. The study was completed in one day.

| Group Number | Composition | Route of Administration | Total Daily Dose of Insulin (μg/animal) | Number of Animals/ Gender |
|---|---|---|---|---|
| 1 | Placebo | i.v. | 0 | 1M |
| 2 | Non-PEG Insulin | i.v. | 20 | 2M |
| 3 | PEG Insulin | i.v. | 20 | 4M |
| 4 | PEG Insulin | i.v. | 40 | 4M |
| 5 | PEG Insulin | i.v. | 30 | 4M |

The results demonstrate that the 5K PEG insulin composition possesses bioactivity, i.e., the insulin molecule remains active upon modification with polyethylene glycol, as can be seen by its ability to lower blood glucose. Mean serum insulin concentrations following i.v. administration of pegylated insulin were dose dependent; a dose dependent decrease in glucose levels was also observed. The results are summarized in FIGS. 2 and 3. FIG. 2 is a plot of mean serum insulin concentrations following i.v. administration of illustrative compositions of pegylated versus non-pegylated insulin; FIG. 3 is a plot of blood glucose concentrations following i.v. administration of the compositions described above.

Example 8

Administration of 5K PEG Insulin to the Lung (P-2001-017)

An exemplary pegylated insulin, 5K PEG insulin, was administered to rats via intratracheal administration to determine (i) whether its activity was maintained upon administration to the lung, and (ii) its impact, if any, on serum insulin and blood glucose concentrations when delivered directly to the lung.

Stock Solutions

Non-PEGylated Insulin: 1 ml of PBS was added to 1.0 mg of insulin powder to prepare a 1 mg/ml stock solution. The stock solution of insulin (control) was prepared on the study initiation day.

5K PEG Insulin: 4.0 ml of PBS was added to 7.8 mg of 5K PEG Insulin powder to prepare a 1 mg/ml (based on insulin) stock solution.

Dosing Solutions

40 μg/animal of Insulin: Within 2 hours of dosing, 667 μl of the insulin stock solution was added to 4.33 ml of PBS.

150 μg/animal of Insulin B-1: Within 2 hours of dosing, 2.5 ml of the 5K PEG Insulin stock solution was added to 2.5 ml of PBS.

Intratracheal Instillation

The rats were lightly anesthetized using inhaled 3.0–5.0% Isoflurane (Abbott Laboratories) mixed with oxygen for approximately 5 minutes in a plexiglass anesthesia chamber. Administration was accomplished by insertion of a gavage needle (Popper & Sons Inc.; 18×3" W2-¼ mm ball, New Hyde Park, N.Y. 11040) fitted into a 1 mL syringe into the mouth of the rat down the trachea to just above the main carina. When inserting the gavage needle into the trachea, proper insertion was detected by feeling for the roughness of the cartilage rings under the skin of the throat using the ball of the gavage needle. Doses were administered into the lungs utilizing this method, and followed by removal of the gavage needle.

Fourteen (N=7/Group) fasted male rats (Hilltop Lab Animals, Scottsdale, Pa. (300–350 g)) with indwelling jugular vein catheters (JVC) were used for this study. Non-pegylated human insulin was administered to Group 1 as a 40 μg/300 μL i.t. dose. The PEGylated human insulin formulation was administered to Group 2 as a 150 μg/300 μL i.t. dose. Blood samples (~500 μL) were collected at predose (2 to 0.25 hours prior to dosing), 15, 30, 60, 120, 240, 360, 480, and 720 minutes postdose. A small amount of blood was placed on a glucose test strip for determination of blood glucose in the Glucometer Elite glucose monitor (Bayer Corp., Elkart, Ind.). The remainder of the sample was placed into serum separator tubes and analyzed by radioimmunoassay. Means and standard deviations (SD) were calculated using Microsoft Excel 2000. Animal 2–3 was dropped from the study due to a clogged catheter.

TABLE 5

Summary of In-Vivo Experiments in Rats
The following are the actual doses administered
and actual animal numbers per
group that were used.

| Group No. | Type of Insulin | Route of Administration | Number of Animals/ Gender | Total Daily Dose of Insulin (μg/animal) | No of Dosing Days |
|---|---|---|---|---|---|
| 1 | Insulin | I.T. | 7M | 40 | 1 |
| 2 | 5K PEG Insulin | I.T. | 7M | 150 | 1 |

TABLE 6

In-Vivo Dose Levels

| Group No. | Type of Insulin | Total Daily Dose of Insulin (μg/animal) | Dose Volume (μl) | Concentration of Dosing Solution (μg/ml) |
|---|---|---|---|---|
| 1 | Insulin | 40 | 300 | 133.33 |
| 2 | 5K PEG Insulin | 150 | 300 | 500 |

Mean serum concentrations and mean blood concentrations of insulin and 5K PEG Insulin following intratracheal administration were plotted and are shown in FIG. 4 and in FIG. 5 respectively. The results demonstrate that the pegylated insulin compositions of the invention possess activity upon delivery to and residence within the lung. The pharmacokinetic data further demonstrate that pegylated insulin not only passes through the lung into the circulation, but does so whilst maintaining activity, as evidenced by detectable serum insulin levels corresponding to non-endogenous insulin. Due to the blood levels of insulin observed within about 1 hour following intratracheal administration, it appears that pegylated insulin is not substantially held up within the lungs and crosses the lungs into the bloodstream shortly after administration. The results further indicate that pegylated insulin, when administered to the lung, is effective in lowering blood glucose. However, in the present example, pegylated insulin appears less effective than non-pegylated insulin at the doses administered in lowering blood glucose. Both the pharmacokinetic and pharmacodynamic response curves for intratracheally administered pegylated insulin somewhat resemble non-pegylated insulin, although based upon the profiles in FIG. 4, PEG-insulin appears to be longer acting than non-pegylated insulin. Further optimization of the dosing amounts and particular polyethylene glycol modifiers may be readily achieved by one of skill in the art, based upon the guidance presented herein and depending upon the dosing requirements, intended patient population, condition to be treated, and the like, of a particular chemically modified insulin product.

Example 9

Administration of 750-1 PEG Insulin to the Lung (P-2001-025)

A representative pegylated insulin, 750-1-PEG Insulin, was administered to rats by intratracheal administration. The study was conducted, in part, to explore the effects of a composition of insulin covalently attached to one or more polyethylene glycol chains having an approximate molecular weight of 1,000 Daltons or less, when administered to the lung.

The in-vivo rat study was conducted essentially as described in Example 8 above. The precise dosing regimen followed and doses administered are summarized in the tables below.

TABLE 7

| Group No. | Type of Insulin | Route of Administration | Number of Animals/ Gender | Total Daily Dose of Insulin ($\mu$g/animal) | No of Dosing Days |
|---|---|---|---|---|---|
| 1 | Insulin | I.T. | 2M | 80 | 1 |
| 2 | 750-1 PEG Insulin | I.T. | 4M | 100 | 1 |
| 3 | 750-1 PEG Insulin | I.T. | 4M | 300 | 1 |
| 4 | 750-1 PEG Insulin | I.T. | 4M | 500 | 1 |

TABLE 8

| Group No. | Type of Insulin | Total Daily Dose of Insulin ($\mu$g/animal) | Dose Volume ($\mu$l) | Concentration of Dosing Solution ($\mu$g/ml) |
|---|---|---|---|---|
| 1 | Insulin | 80 | 300 | 266.67 |
| 2 | 750-1 PEG Insulin | 100 | 300 | 333.33 |
| 3 | 750-1 PEG Insulin | 300 | 300 | 1000.00 |
| 4 | 750-1 PEG Insulin | 500 | 300 | 1666.67 |

Serum insulin and blood glucose concentrations of insulin and 750-1 PEG Insulin following intratracheal administration in rats were plotted and are shown in FIG. 6 and FIG.7 respectively. When looking at the plot of mean serum insulin concentrations in FIG. 6, native or non-pegylated insulin reached its maximum serum concentration at approximately 15 minutes, while the pegylated insulin compositions reached maximum serum concentrations at 6 hours (100 $\mu$g/animal) and 8 hours (300 $\mu$g/animal), demonstrating the long-acting nature of these compositions when administered to the lung by inhalation. As can be seen in FIG. 6, unmodified insulin returned to baseline at approximately 6 hours post administration while the insulin levels for pegylated insulin at 6 hours were significantly above baseline (from about 3 to 7 times or greater the baseline value). Moreover, intratracheal administration of pegylated insulin resulted in sustained levels of systemic insulin that had not returned to baseline even at 12 hours post administration. In fact, insulin levels for pegylated insulin were over three times the baseline value (i.e., the value for non-modified insulin) at both 8 and 12 hours. A plot of these results is shown in FIG. 6.

In sum, when administered to the lung, 750-1 PEG insulin resulted in increased systemic insulin levels when compared to unmodified insulin. Moreover, systemic insulin levels for the pegylated insulin group were still significantly above baseline even at 12 hours. That is to say, elevated insulin levels were sustained for the pegylated insulin group for at least twice as long as for unmodified insulin. This data further demonstrates that pegylated insulin crosses the lungs, is bioactive, and provides prolonged systemic levels of insulin when compared to unmodified insulin.

A plot of mean blood glucose concentrations following intratracheal administration of non-pegylated versus 750-1 pegylated insulin is provided in FIG. 7. Blood glucose response levels correlated nicely with serum insulin levels for the pegylated insulin group. (That is to say, at elevated levels of serum insulin, a corresponding supression/lowering of blood glucose was also observed). In looking at FIG. 7, it can be seen that the pegylated insulin compositions of the invention, when administered orally to the lung, exhibit a rapid onset of action comparable to native insulin rather than a delayed onset of action typical of many sustained release formulations. That is to say, suppression of glucose occurs shortly after administration. Additionally, while native or non-pegylated insulin reaches maximum glucose lowering in about 2 hours, the time to reach maximum glucose lowering for pegylated insulin was extended to at least 4 hours, 6 hours and 8 hours for the 500 $\mu$g, 100 $\mu$g, and 300 $\mu$g doses, respectively. So, the time to reach maximum blood glucose lowering for pegylated insulin, when administered to the lung, was prolonged 2 to 4 times over that of non-pegylated insulin. Overall, the 750-1 PEG insulin glucose suppression was significantly increased over the 12 hour period when compared with unmodified insulin. At 8 hours, glucose levels had essentially returned to normal for unmodified insulin, while glucose levels for the PEG insulin group were from 1.3 to 3 times lower than for unmodified insulin. Glucose levels for the pegylated insulin group had not returned to even at 12 hours, further indicating prolonged glucose suppression for the lly derivatized insulin compositions of the present invention.

Example 10

Administration of 750-1 PEG Insulin to the Lung (P-2002-001)

In a study similar to Example 9 above, 750-1-PEG insulin was administered to intratracheal administration at doses lower than those employed in Example 9.

The in-vivo intratracheal rat study was conducted essentially as described in Example 8 above. The precise dosing regimen and doses administered are summarized in the tables below.

TABLE 9

| Group No. | Type of Insulin | Route of Administration | Number of Animals/ Gender | Total Daily Dose of Insulin (µg/animal) | No of Dosing Days |
|---|---|---|---|---|---|
| 1 | Insulin | i.t. | 5M | 80 | 1 |
| 2 | 750-1 PEG Insulin | i.t. | 5M | 80 | 1 |
| 3 | 750-1 PEG Insulin | i.t | 5M | 160 | 1 |

TABLE 10

| Group No. | Type of Insulin | Total Daily Dose of Insulin (µg/animal) | Dose Volume (µl) | Concentration of Dosing Solution (µg/ml) |
|---|---|---|---|---|
| 1 | Insulin | 80 | 300 | 266.7 |
| 2 | 750PEG Insulin-1 | 80 | 300 | 266.7 |
| 3 | 750PEG Insulin-1 | 160 | 300 | 533.3 |

Serum insulin and blood glucose concentrations of unmodified insulin and 750-1 PEG insulin following intratracheal administration in rats were plotted and the results are shown in FIG. 8 and in FIG. 9, respectively. When looking at the plot of mean serum insulin concentrations in FIG. 8, native or non-pegylated insulin reached its maximum serum concentration at approximately 15 minutes, while the pegylated insulin compositions reached maximum serum concentrations at 2 hours (80 µg/animal) and 6 hours (160 µg/animal). That is to say, the time to reach maximum serum levels of insulin for peg-modified insulin was extended 8 to 24 times over native or non-pegylated insulin when administered to the systemic circulation via the lung. As can be seen in FIG. 8, unmodified insulin returned to baseline at approximately 12 hours post administration, while insulin levels for the PEG-insulin group ranged from 2.5 to 3.5 times the baseline value at the same 12 hour time point. Insulin levels for the pegylated insulin group did not return to baseline until around 25 hours, meaning that it took twice as long for the pegylated insulin group to return to baseline when compared to unmodified insulin. Systemic insulin levels were sustained for the pegylated insulin group for a duration of time about two-fold or twice (25 hours versus 12 hours) that of unmodified insulin. At time points up to about 6 hours, the insulin levels for the two pegylated insulin groups roughly corresponded to the doses administered (that is to say, insulin concentrations for the 160 µg/animal group were approximately twice those of the 80 µg/animal group).

A plot of mean blood glucose concentrations following intratracheal administration of non-pegylated versus 750-1 pegylated insulin is provided in FIG. 9. At 25 hours post administration, glucose suppression for both pegylated insulin groups had still not returned to baseline in contrast to unmodified insulin. Similar to the results from Example 9, the overall profiles for pegylated insulin demonstrate prolonged glucose suppression extending beyond 25 hours. At 8 hours, glucose levels had returned to nearly normal for unmodified insulin while glucose levels for the PEG insulin groups were about 1.5 times lower than for unmodified insulin. These results further demonstrate that modifying insulin with one or more polyethylene glycol moieties results in good bioavailability across the lungs and prolonged systemic insulin levels as well as prolonged glucose suppression.

Example 11

Administration of 750-2 PEG Insulin to the Lung (P-2002-003)

A representative pegylated insulin composition, 750-2-PEG insulin, was administered to rats by intratracheal administration. This study was conducted to further explore the effect of various doses of pegylated versus non-pegylated insulin when administered directly to the lungs. Animals were dosed at 80 µg insulin per animal for both pegylated and non-pegylated forms of insulin. The in-vivo rat study was conducted essentially as described in Example 8 above. The precise dosing regimen followed and doses administered are summarized in the tables below.

TABLE 11

| Group No. | Type of Insulin | Route of Administration | Number of Animals/ Gender | Total Daily Dose of Insulin (µg/animal) | No of Dosing Days |
|---|---|---|---|---|---|
| 1 | Insulin | IT | 7M | 80 | 1 |
| 2 | 750PEG-2 Insulin | IT | 7M | 80 | 1 |

TABLE 12

| Group No. | Type of Insulin | Total Daily Dose of Insulin (µg/animal) | Dose Volume (µl) | Concentration of Dosing Solution (µg/ml) |
|---|---|---|---|---|
| 1 | Insulin | 80 | 300 | 266.7 |
| 2 | 750PEG-2 Insulin | 80 | 300 | 266.7 |

A plot of mean serum insulin concentrations following intratracheal instillation of both non-pegylated and 750-1 PEG insulin at a dose of 80 µg/animal is shown in FIG. 10. A plot of mean blood glucose concentrations following intratracheal instillation of both non-pegylated and 750-1 PEG insulin at a dose of 80 µg/animal is shown in FIG. 11. Results similar to those in Examples 9 and 10 were obtained.

A tabulation of pharmacokinetic parameters from Examples 10 and 11 is provided below. Bioavailability is absolute bioavailability (i.e., compared to intraveneously administered insulin).

TABLE 13

Mean Serum Insulin Pharmacokinetics

| Example | Type of Insulin | Route | Dose µg/ animal | $C_{Max}$ µU/ml | $T_{Max}$ min | AUC µU* min/ ml | Absolute BA |
|---|---|---|---|---|---|---|---|
| 9 (P-2001-25) | Insulin | IT | 80 | 56 | 15 | 12878 | |
| 9 | 750-1 PEG | IT | 100 | 64 | 368 | 27954 | |
| 9 | 750-1 PEG | IT | 300 | 160 | 188 | 50691 | |
| 9 | 750-1 PEG | IT | 500 | 3474 | 184 | 255881 | |

TABLE 13-continued

Mean Serum Insulin Pharmacokinetics

| Example | Type of Insulin | Route | Dose μg/ animal | $C_{Max}$ μU/ml | $T_{Max}$ min | AUC μU* min/ ml | Absolute BA |
|---|---|---|---|---|---|---|---|
| 10 (P-2002-001) | Insulin | IT | 80 | 132 | 15 | 28167 | |
| 10 | 750-1 PEG | IT | 80 | 56 | 210 | 36818 | |
| 10 | 750-1 PEG | IT | 160 | 117 | 78 | 60713 | |
| IV Ref. P-2002-002 | Insulin | IV | 20 | 3057 | 5 | 44388 | |
| IV Ref. | 750-2 PEG | IV | 20 | 2638 | 7 | 63190 | |
| IV Ref. | 750-2 PEG | IV | 30 | 3510 | 5 | 62746 | |
| 11 (P-2002-003) | insulin | IT | 80 | 89 | 24 | 22203 | 12.5 |
| 11 | 750-2 PEG | IT | 80 | 164 | 73 | 57639 | 32** 32*** |

*outlier was not removed from data set.
**relative to IV 20 μg/animal dose. Value with outlier removed was 22%
***relative to IV 30 μg/animal dose. Value with outlier removed was unchanged.

Absolute bioavailability was calculated as follows:

$$\frac{(AUC)}{(AUC_{IV\,ins})} \frac{(Dose_{IV\,ins})}{(Dose)}$$

Example 12

Administration of 2K PEG Insulin to the Lung (P-2002-010)

Another exemplary pegylated insulin composition, 2K PEG insulin, was administered to rats by intratracheal administration. The 2K PEG insulin used for this study was prepared as described in Example 3. Animals were dosed at 80 μg insulin per animal for non-pegylated insulin. Animals were dosed at 300 μg insulin per animal, 600 μg insulin per animal, 900 μg insulin per animal, and 1200 μg insulin per animal for 2K PEG insulin. The in-vivo rat study was conducted essentially as described in Example 8 above. The precise dosing regimen followed and doses administered are summarized in the tables below.

TABLE 14

| Group No. | Type of Insulin | Route of Administration | Number of Animals/ Gender | Total Daily Dose of Insulin (μg/animal) | No of Dosing Days |
|---|---|---|---|---|---|
| 1 | Insulin | i.t. | 3 | 80 | 1 |
| 2 | PEG2K-1 Insulin | i.t. | 3 | 600 | 1 |
| 3 | PEG2K-1 Insulin | i.t. | 3 | 80 | 1 |
| 4 | PEG2K-1 Insulin | i.t. | 3 | 160 | 1 |
| 5 | PEG2K-1 Insulin | i.t. | 3 | 300 | 1 |
| 6 | PEG2K-1 Insulin | i.t. | 3 | 900 | 1 |
| 7 | PEG2K-1 Insulin | i.t. | 3 | 1200 | 1 |

TABLE 15

| Group No. | Type of Insulin | Total Daily Dose of Insulin (μg/animal) | Dose Volume (μl) | Concentration of Dosing Solution (mg/ml) |
|---|---|---|---|---|
| 1 | Insulin | 80 | 300 | 0.267 |
| 2 | PEG2K-1 Insulin | 600 | 300 | 2.0 |
| 3 | PEG2K-1 Insulin | 80 | 300 | 0.267 |
| 4 | PEG2K-1 Insulin | 160 | 300 | 0.533 |
| 5 | PEG2K-1 Insulin | 300 | 300 | 1.0 |
| 6 | PEG2K-1 Insulin | 900 | 300 | 3.0 |
| 7 | PEG2K-1 Insulin | 1200 | 300 | 4.0 |

A plot of mean blood glucose concentrations following intratracheal administration is shown in FIG. 12. Good dose response was observed for the pegylated insulin compositions when administered to the lung (i.e., higher doses of 2K PEG insulin resulted in a greater decrease in blood glucose concentration). Although the time point in the curve at which maximum glucose suppression was achieved appears to be about 3 hours for both the pegylated and non-pegylated compositions, the profiles for the pegylated versus non-pegylated insulin differ significantly with respect to duration of glucose suppression. In particular, for time points past about 6 hours, at the three higher 2K pegylated insulin doses (600 μg, 900 μg, and 1200 μg per animal), glucose levels were suppressed significantly below those of non-pegylated insulin. These results further demonstrate that a prolonged systemic effect can be achieved by administration of pegylated insulin to the lung.

Example 13

Evaluation of Serum Glucose and Insulin Concentrations Following Intravenous Administration of 2K PEG Insulin in Rats (P-2002-009)

This study was conducted to further explore the activity of insulin in an exemplary 2K PEG insulin composition, and to determine the intravenous (i.v.) dose of pegylated human insulin (PEG2K-1) effective to lower blood glucose to a concentration of about 30–40 mg/dL.

A protocol similar to that described in Example 7 was conducted using the compositions, animal groups, and doses summarized in the tables below.

TABLE 16

| Group No. | Type of Insulin | Route of Administration | Number of Animals/ Gender | Total Daily Dose of Insulin (µg/animal) | No of Dosing Days |
|---|---|---|---|---|---|
| 1 | Insulin | i.v. | 2M | 20 | 1 |
| 2 | PEG2K-1 Insulin | i.v. | 2M | 20 | 1 |
| 3 | PEG2K-1 Insulin | i.v. | 2M | 30 | 1 |
| 4 | PEG2K-1 Insulin | i.v. | 2M | 40 | 1 |
| 5 | PEG2K-1 Insulin | i.v. | 2M | 80 | 1 |
| 6 | PEG2K-1 Insulin | i.v. | 2M | 160 | 1 |

TABLE 17

| Group No. | Control/ Test Article | Total Daily Dose of Insulin (µg/animal) | Dose Volume (µl) | Concentration of Dosing Solution (□g/ml) |
|---|---|---|---|---|
| 1 | Insulin | 20 | 300 | 67 |
| 2 | PEG2 K-1 Insulin | 20 | 300 | 67 |
| 3 | PEG2 K-1 Insulin | 30 | 300 | 100 |
| 4 | PEG2 K-1 Insulin | 40 | 300 | 133 |
| 5 | PEG2 K-1 Insulin | 80 | 300 | 267 |
| 6 | PEG2 K-1 Insulin | 160 | 300 | 533 |

A plot of mean serum insulin concentrations following intravenous administration of non-pegylated and 2K PEG insulin at doses of 20 µg/animal (non-pegylated insulin) and 20, 30 and 40 µg/animal (2K PEG insulin) is shown in FIG. 13. A plot of mean blood glucose concentrations following intravenous administration of non-pegylated and 2K PEG insulin at the doses described above is shown in FIG. 14.

What is claimed is:

1. A dry powder composition for pulmonary administration, said composition comprising a conjugate of insulin covalently coupled to one or more molecules of polyethylene glycol, wherein said powder (i) is characterized by having an emitted dose value of at least about 50% and (ii) when administered to a subject by inhalation, sustains elevated blood levels of insulin in said subject for at least about 6 hours post administration.

2. The composition of claim 1, wherein said polymer is absent a fatty acid moiety.

3. The composition of claim 1, characterized by an absolute pulmonary bioavailability that is greater than that of native insulin.

4. The composition of claim 3, characterized by an absolute pulmonary bioavailability that is at least twice that of native insulin.

5. The composition of claim 1, characterized by an absolute pulmonary bioavailability greater than 15%.

6. The composition of claim 5, characterized by an absolute pulmonary bioavailability greater than 30%.

7. The composition of claim 1, which when administered to the lung, is characterized by a Tmax that is at least three times that of native insulin.

8. The composition of claim 7 which when administered to the lung, is characterized by a Tmax that is at least five tints that of native insulin.

9. The composition of claim 1, wherein said polyethylene glycol is end-capped.

10. The composition of claim 9, wherein said polyethylene glycol is end-capped with an alkoxy group.

11. The composition of claim 1, wherein said polyethylene glycol is selected from the group consisting of linear polyethylene glycol, branched polyethylene glycol, forked polyethylene glycol, and dumbbell polyethylene glycol.

12. The composition of claim 11, wherein said polyethylene glycol comprises a biodegradable linkage.

13. The composition of claim 11, wherein said polyethylene glycol comprises a number of ($OCH_2CH_2$) subunits selected from the group consisting of from about 2 to 300 subunits, from about 4 to 200 subunits, and from about 10 to 100 subunits.

14. The composition of claim 11, wherein said polyethylene glycol has a nominal avenge molecular weight from about 200 to about 4000 daltons.

15. The composition of claim 11, wherein said polyethylene glycol is linear.

16. The composition of claim 14, wherein said polyethylene glycol has a nominal average molecular weight selected from the group consisting of 200, 300, 400, 500, 600, 750, 1000, 1500, 2000, 2500, 3000, 3500, and 4000 daltons.

17. The composition of claim 14, wherein said polyethylene glycol has a nominal average molecular weight from about 200 to about 2,000 daltons.

18. The composition of claim 14, wherein said polyethylene glycol has a nominal average molecular weight from about 200 to about 1,000 daltons.

19. The composition of claim 1, wherein said insulin is native insulin.

20. The composition of claim 1, wherein said conjugate has a purity of greater than 90%.

21. The composition of claim 1, wherein said insulin is covalently coupled to polyethylene glycol at one or more of its amino sites.

22. The composition of claim 21, wherein at least about 75% of the B-1Phe sites on Insulin are covalently coupled to polyethylene glycol.

23. The composition of claim 22, wherein at least about 90% of the B-1Phe sites on insulin are covalently coupled to polyethylene glycol.

24. The composition of claim 21, comprising a mixture of mono-PEG substituted and di-PEG substituted and di-PEG substituted conjugates of insulin.

25. The composition of claim 24, further comprising a tri-PEG substituted conjugate of insulation.

26. The composition of claim 1, wherein said insulin is covalently coupled to polyethylene glycol via a linking moiety positioned at a terminus of said polyethylene glycol.

27. The composition of claim 1, wherein said polyethylene glycol, prior to coupling with insulin, possesses an activated linking moiety at one terminus suitable for covalent coupling with insulin.

28. The composition of claim 27, wherein said activated linking moiety is suitable for coupling with reactive insulin amino groups.

29. The composition of claim 28, wherein said activated linking moiety comprises a reactive functional group selected from the group consisting of N-hydroxysuccinimide active esters, active carbonates, aldehydes, and acetals.

30. The composition of claim 26, wherein insulin is covalently coupled to polyethylene glycol via an amide linkage.

31. The composition of claim 1 in aerosolized form.

32. The composition of claim 1 in liquid or dry form.

33. The composition of claim 1 further comprising a pharmaceutically acceptable excipient.

34. The composition of claim 1 in spray-dried form.

35. The composition of claim 1, having a $T_g$ greater than 50° C.

36. The composition of claim 1, comprising from 2% to 95% by weight PEG-insulin conjugate.

37. The composition of claim 33, wherein said excipient is selected from the group consisting of carbohydrates, amino acids, dipeptides, tripeptides, and buffers.

38. The composition of claim 37, wherein said excipient is a di- or tripeptide containing two or more leucyl residues.

39. The composition of claim 1 having an MMD of less than 10 μm.

40. The composition of claim 1, having an MMD of less than 4 μm.

41. The composition of claim 1, having an MMAD of less than 5 μm.

42. The composition of claim 1, having an MMAD of less than 3.5 μm.

43. The composition of claim 1, having a moisture content of less than 10% by weight.

44. The composition of claim 1, in a dosage receptacle.

* * * * *